(12) United States Patent
Sekimoto

(10) Patent No.: US 8,305,564 B2
(45) Date of Patent: Nov. 6, 2012

(54) METHOD FOR AUTOMATICALLY DISCRIMINATING CONTROL SOLUTION

(75) Inventor: Shinjirou Sekimoto, Kyoto (JP)

(73) Assignee: Arkray, Inc., Kyoto (JP)

( * ) Notice: Subject to any disclaimer, the term of this patent is extended or adjusted under 35 U.S.C. 154(b) by 595 days.

(21) Appl. No.: 12/227,406

(22) PCT Filed: May 16, 2007

(86) PCT No.: PCT/JP2007/060078
§ 371 (c)(1),
(2), (4) Date: Sep. 21, 2009

(87) PCT Pub. No.: WO2007/132903
PCT Pub. Date: Nov. 22, 2007

(65) Prior Publication Data
US 2010/0014085 A1 Jan. 21, 2010

(30) Foreign Application Priority Data
May 16, 2006 (JP) .................................. 2006-137084

(51) Int. Cl.
*G01N 33/48* (2006.01)
(52) U.S. Cl. ........................................................ 356/39
(58) Field of Classification Search ............... 356/39, 356/436
See application file for complete search history.

(56) References Cited

U.S. PATENT DOCUMENTS
7,670,846 B2 * 3/2010 Frey et al. ..................... 436/164

FOREIGN PATENT DOCUMENTS
| JP | 63-243879 A | 10/1988 |
| JP | 08-015243 A | 1/1996 |
| JP | 10-339732 A | 12/1998 |
| JP | 2001-208718 A | 8/2001 |
| JP | 2002-039922 A | 2/2002 |
| JP | 2003-114214 A | 4/2003 |
| JP | 2005-531760 A | 10/2005 |
| JP | 2006-053164 A | 2/2006 |

OTHER PUBLICATIONS

International Search Report mailed on Jun. 12, 2007.
Office Action issued in related Japanese application No. 2008-515596, dated May 15, 2012.

* cited by examiner

*Primary Examiner* — Tarifur Chowdhury
*Assistant Examiner* — Abdullahi Nur
(74) *Attorney, Agent, or Firm* — Rader, Fishman & Grauer PLLC

(57) ABSTRACT

The present invention relates to a method for automatically discriminating a control solution from a sample in a measurement system for measuring a target ingredient in the sample by using a measurement wavelength and a reference wavelength, wherein as the control solution, a control solution having a response value lower than a lower limit value (threshold) of a response value, such as absorbance, supposed when luminance of the sample is measured at the reference wavelength and having a response value higher than an upper limit value (threshold) of a response value supposed when luminance of the sample is measured at the detection wavelength for detecting whether the sample is supplied is used.

17 Claims, 15 Drawing Sheets

Reference wavelength

Detection wavelength

Detection wavelength

METHOD FOR AUTOMATICALLY DISCRIMINATING CONTROL SOLUTION

TECHNICAL FIELD

The present invention relates to a technique for automatically discriminating a control solution from a sample in a measurement system for measuring a target ingredient in the sample.

BACKGROUND ART

It is important for discovery and treatment of various diseases to know biological information such as glucose concentration in blood. In order to determine the biological information in blood, a method using an analytical tool such as a biosensor is known. This method involves supplying a reagent layer in the analytical tool with a blood sample, and detecting information corresponding to a concentration of a target ingredient in the blood sample based on a reaction product as a result of reaction of the blood sample with a reagent, in a concentration measuring apparatus using an optical method or an electrochemical method.

In such a concentration measuring apparatus, it is necessary to check whether or not the apparatus operates normally to ensure reliability of a measurement result when the apparatus has not been used for a long time, or every certain period. Usually, a check of a concentration measuring apparatus is performed by a user by installing an analytical tool in the apparatus while manually selecting a control solution measurement mode by operating the concentration measuring apparatus, and supplying the analytical tool with a control solution.

In such a method, the user needs not only to make operation for carrying out an operation check of the apparatus, but also to make operation for returning the apparatus to a normal measurement mode after completion of the operation check of the apparatus, and hence has a big burden. This may lead a situation that the apparatus is checked without switching the mode from the normal measurement mode to the control solution measurement mode, or that the sample is measured without switching the mode from the control measurement mode to the normal measurement mode. As a result of this, a correct check result or measurement result is not obtained, and the necessity of recheck or re-measurement may arise.

In order to solve such a drawback, it has been proposed to automatically recognize a control solution and to check the apparatus in a concentration measuring apparatus (see, Patent documents 1 to 3, for example).

The method described in Patent document 1 focuses on a difference in solubility between whole blood and control solution in a reagent layer, and discriminates the control solution from the whole blood based on profiles of reflectance. This method is applied to a measurement system utilizing an optical technique, and a control solution containing an IR pigment having maximum absorption at a wavelength different from a measurement wavelength is used, discrimination between whole blood and a control solution is made at a wavelength different from the measurement wavelength.

In Patent document 1, there is also disclosed a method for discriminating a control solution from whole blood based on a difference in a measured current value between the whole blood and the control solution in a measurement system using an electrochemical technique.

In Patent document 2, likewise Patent document 1, there is disclosed a method for discriminating a control solution from whole blood based on profiles of reflectance in a measurement system using an optical technique, and also disclosed a method for discriminating a control solution from whole blood based on a difference in a measured current value in a measurement system using an electrochemical technique.

In the method described in Patent document 3, for an electrode-type biosensor, a detection electrode is provided in addition to an active electrode and a counter electrode, and a control solution is automatically discriminated based on oxidation current obtained by using the detection electrode, in a measurement system using an electrochemical technique. The methods of the foregoing documents focus on a fact that behavior of the oxidation current obtained when the control solution reacts with the reagent layer of the biosensor differs from behavior of the oxidation current obtained when the sample reacts with the reagent layer, and automatically discriminates the control solution from the sample based on an oxidation current value after a lapse of a predetermined time, or time-varying change in an oxidation current value.

However, the method for discriminating a control solution based on profile of reflectance as described in Patent documents 1 and 2 will be influenced by solubility in the reagent layer or reaction speed. On the other hand, since solubility in the reagent layer or reaction speed vary between different biosensors, and may vary during the period from production till use. When whole blood is used as a sample, reflectance will be influenced by a hematocrit value of the whole blood. Therefore, in the method for discriminating a control solution based on profile of reflectance, it is difficult to accurately discriminate the control solution.

Further, the method for discriminating a control solution based on a measured current value in a measurement system using an electrochemical technique is not applicable to a measurement system using an optical technique.

Patent document 1: Japanese Patent Application Laid-Open Publication No. 2003-114214

Patent document 2: Japanese Patent Application Laid-Open Publication No. 2005-531760 patent document 3: Japanese Patent Application Laid-Open Publication No. 2001-208718

DISCLOSURE OF THE INVENTION

Problem to be Solved by the Invention

It is an object of the present invention to provide a technique capable of mitigating a burden on a measurer to automatically discriminate a control solution, while preventing occurrence of erroneous measurement, and capable of accurately discriminating a control solution, and applicable to both measurements systems using an optical technique and an electrochemical technique.

Means for Solving the Problem

In a first aspect of the present invention, there is provided a method for automatically discriminating a control solution from a sample in a measurement system for measuring a target ingredient in the sample, wherein as the control solution, a solution having, outside a range between an upper limit value and a lower limit value of a response value supposed when the sample is measured with light of a specific wavelength, a response value at the specific wavelength is used.

As the control solution, for example, when the response value is absorbance, a solution having a response value (absorbance) lower than the lower limit value of the response value (absorbance) supposed when luminance of the sample is measured at the reference wavelength, a solution having a response value (absorbance) higher than the upper limit value of the response value (absorbance) supposed when the luminance of the sample is measured at the detection wavelength or a solution having a response value (absorbance) lower than the lower limit value of the response value (absorbance) supposed when the luminance of the sample is measured at the reference wavelength and having a response value (absorbance) higher than the upper limit value of the response value (absorbance) supposed when the luminance of the sample is measured at the detection wavelength is used.

Preferably, the automatic discrimination method of the present invention includes: a first step of measuring luminance of a liquid to be detected at the detection wavelength; a second step of determining whether or not a response value (absorbance) of the liquid to be detected at the detection wavelength is equal to or higher than the upper limit value; a third step of measuring the luminance of the liquid to be detected at the detection wavelength when it is determined in the second step that the response value (absorbance) of the liquid to be detected at the detection wavelength is equal to or higher than the upper limit value; a fourth step of determining whether or not the response value (absorbance) of the liquid to be detected at the reference wavelength is lower than the lower limit value; and a fifth step of discriminating the liquid as a control solution when it is determined in the fourth step that the response value (absorbance) of the liquid to be detected at the reference wavelength is lower than the lower limit value.

In the measurement system to which the present invention is applicable, for example, whole blood is used as a sample, and the detection wavelength is selected from a wavelength range of 500 to 600 nm, the measurement wavelength is selected from a wavelength range of 600 to 700 nm, and the reference wavelength is selected from a wavelength range of 700 to 950 nm, preferably from a wavelength range of 800 to 950 nm. In this case, as the control solution, for example, a solution containing a red pigment, and having a maximum absorption wavelength within a wavelength range of 500 to 600 nm is used.

As the red pigment, for example, at least one selected from 6-hydroxy-5-(2-methoxy-5-methyl-4-sulfophenylazo)-2-naphthalene sulfonic acid, 7-hydroxy-8-(4-sulfonaphthylazo)-1,3-naphthalene disulfonic acid, and 3',6'-bis(diethylamino)spiro [3H-2,1-benzoxathiol-1,1-dioxide-3,9'-[9H] xanthene]-6-sulfonic acid is used.

As the control solution, a solution having a response value (absorbance) higher than the upper limit value of the response value (absorbance) supposed when luminance of a sample is measured at the reference wavelength, for example, a solution containing an IR pigment having high light absorption in a near infrared region may be used.

As the control solution, a plurality of control solutions having different concentrations of the target ingredient may be used. In this case, as the control solutions, for example, a low concentration control solution having a relatively low concentration of the target ingredient, a high concentration control solution having a relatively large concentration of the target ingredient, and a medium concentration control solution having an intermediate concentration of the target ingredient between those of the low concentration control solution and the high concentration control solution may be used.

Preferably, the automatic discrimination method of the present invention includes: a first step of measuring concentration of the target ingredient in the liquid to be detected at the measurement wavelength; a second step of measuring response of the liquid to be detected by the detection wavelength; a third step of selecting a corresponding response threshold from a plurality of response thresholds set in advance, according to the concentration of the target ingredient measured in the first step; and a fourth step of determining whether or not the liquid to be detected is a control solution by comparing the response measured in the second step and the response threshold selected in the third step.

The third step is performed by selecting a response threshold correlated with a particular classification that the concentration of the target ingredient measured in the first step is determined to belong among a plurality of concentration regions classified by the predetermined concentration thresholds.

The concentration thresholds include, for example, a first concentration threshold which is a concentration between the concentration of the target ingredient in the low concentration control solution and the concentration of the target ingredient in the medium concentration control solution, and a second concentration threshold which is a concentration between the concentration of the target ingredient in the medium concentration control solution and the concentration of the target ingredient in the high concentration control solution.

The response threshold includes, for example, a first response threshold for use when the concentration measured in the first step is lower than the first concentration threshold, a second response threshold for use when the concentration measured in the third step is equal to or higher than the first concentration threshold and lower than the second concentration threshold, and a third response threshold for use when the concentration measured in the first step is equal to or higher than the second concentration threshold.

In a second aspect of the present invention, there is provided a control solution which is used for checking a system in a measurement system for measuring a target ingredient in a sample, and has, outside a range between an upper limit value and a lower limit value of a response value supposed when luminance of the sample is measured with light of a specific wavelength, a response value at the specific wavelength.

In a measurement system for measuring a target ingredient in a sample by using a measurement wavelength and a reference wavelength, when the response value is absorbance, for example, as the control solution, for example, a solution having a response value (absorbance) lower than the lower limit value of the response value (absorbance) supposed when luminance of the sample is measured at the reference wavelength is used.

In a measurement system capable of detecting whether or not a sample is supplied by using a detection wavelength, as the control solution, for example, a solution having a response value (absorbance) higher than the upper limit value of the response value (absorbance) supposed when luminance of the sample is measured at the detection wavelength is used.

In a measurement system for measuring a target ingredient in a sample by using a measurement wavelength and a reference wavelength, and capable of detecting whether or not the sample is supplied by using a detection wavelength, as the control solution, for example, a solution having a response value (absorbance) lower than the lower limit value of the response value (absorbance) supposed when luminance of the sample is measured at the reference wavelength and having a response value (absorbance) higher than the upper limit value of the response value (absorbance) supposed when the luminance of the sample is measured at the detection wavelength is used.

The control solution of the present invention is used in a measurement system in which whole blood is used as a sample, and the detection wavelength is selected from a wavelength range of 500 to 600 nm, the measurement wavelength is selected from a wavelength range of 600 to 700 nm, and the reference wavelength is selected from a wavelength range of 700 to 950 nm, preferably from a wavelength range of 800 to 950 nm. In this case, as the control solution, for example, a solution containing a red pigment, and having a maximum absorption wavelength within a wavelength range of 500 to 600 nm is used.

As the red pigment, for example, at least one selected from 6-hydroxy-5-(2-methoxy-5-methyl-4-sulfophenylazo)-2-naphthalene sulfonic acid, 7-hydroxy-8-(4-sulfonaphthylazo)-1,3-naphthalene disulfonic acid, and 3',6'-bis(diethylamino) spiro [3H-2,1-benzoxathiol-1,1-dioxide-3,9'-[9H] xanthene]-6-sulfonic acid is used.

In the measurement system for measuring a target ingredient in a sample by using a measurement wavelength and a reference wavelength, the control solution may have a response value (absorbance) higher than the upper limit value of the response value (absorbance) supposed when luminance of the sample is measured at the reference wavelength. In this case, the control solution is a solution containing, for example, an IR pigment having high light absorption in a near infrared region.

In a third aspect of the present invention, there is provided a measuring apparatus for measuring a target ingredient in a sample at a measurement wavelength and a reference wavelength, and capable of detecting whether or not the sample is supplied by using a detection wavelength, which is configured to check the apparatus by using a control solution, wherein when a response value is absorbance, it is determined that the control solution is supplied when at least one of the following conditions is satisfied.

(1) When the response value (absorbance) is lower than a lower limit value of response value (absorbance) supposed when luminance of the sample is measured at the reference wavelength, or when information from which it is determined that the response value (absorbance) is lower than the lower limit value is obtained;

(2) When the response value (absorbance) is higher than an upper limit value of the response value (absorbance) supposed when the luminance of the sample is measured at the detection wavelength, or when information from which it is determined that the response value (absorbance) is higher than the upper limit value is obtained; and (3) When the response value (absorbance) is higher than the upper limit value of the response value (absorbance) supposed when the luminance of the sample is measured at the reference wavelength, or when information from which it is determined that the response value (absorbance) is higher than the upper limit value is obtained.

Preferably, the measuring apparatus according to the present invention is configured to execute: a first step of measuring luminance of a liquid to be detected at the detection wavelength; a second step of determining whether or not a response value (absorbance) of the liquid to be detected at the detection wavelength is equal to or higher than the upper limit value; a third step of measuring the luminance of the the liquid to be detected at the reference wavelength when it is determined in the second step that the absorbance of the liquid to be detected at the detection wavelength is equal to or higher than the upper limit value; a fourth step of determining whether or not the response value (absorbance) of the liquid to be detected at the reference wavelength is lower than the lower limit value; and a fifth step of discriminating the liquid as a control solution when it is determined in the fourth step, that the absorbance of the liquid to be detected at the reference wavelength is lower than the lower limit value, in order to determine whether or not the control solution is supplied.

The measuring apparatus according to the present invention is configured to measure a target ingredient using, for example, whole blood as a sample, and employs a wavelength range of 500 to 590 nm as the detection wavelength, a wavelength range of 600 to 700 nm as the measurement wavelength and a wavelength range of 700 to 950 nm, preferably a wavelength range of 800 to 950 nm as the reference wavelength.

In a fourth aspect of the present invention, there is provided a measuring apparatus for measuring a target ingredient in a sample by using a measurement wavelength and capable of detecting whether or not the sample is supplied by using a detection wavelength, which is configured to check the apparatus using a control solution, the measuring apparatus being configured to execute the following steps when a response value is a light receiving amount.

(1) A first step of measuring concentration of the target ingredient in the liquid to be detected at the measurement wavelength;

(2) a second step of measuring response of the liquid to be detected at the detection wavelength;

(3) a third step of selecting a corresponding response threshold from a plurality of response thresholds set in advance, according to the concentration of the target ingredient measured in the first step; and (4) a fourth step of determining whether or not the liquid to be detected is a control solution by comparing the response measured in the second step and the response threshold selected in the third step.

When a plurality of control solutions having different concentrations of target ingredients are used as the control solutions, the third step is performed by selecting a response threshold correlated with a particular classification that the concentration of the target ingredient measured in the first step is determined to belong among a plurality of concentration regions classified by the predetermined concentration thresholds.

In a case where a low concentration control solution having a relatively low concentration of target ingredient, a high concentration control solution having a relatively large concentration of target ingredient, and a medium concentration control solution having an intermediate concentration of target ingredient between those of the low concentration control solution and the high concentration control solution are used as the control solutions, the concentration thresholds include, for example, a first concentration threshold which is a concentration between the concentration of the target ingredient in the low concentration control solution and the concentration of target ingredient in the medium concentration control solution, and a second concentration threshold which is a concentration between the concentration of the target ingredient in the medium concentration control solution and the concentration of the target ingredient in the high concentration control solution.

The response threshold includes, for example, a first response threshold for use when the concentration measured in the first step is lower than the first concentration threshold, a second response threshold for use when the concentration measured in the third step is equal to or higher than the first concentration threshold and lower than the second concentration threshold, and a third response threshold for use when the concentration measured in the first step is equal to or higher than the second concentration threshold.

BRIEF DESCRIPTION OF THE DRAWINGS

[1]

Figure 1:
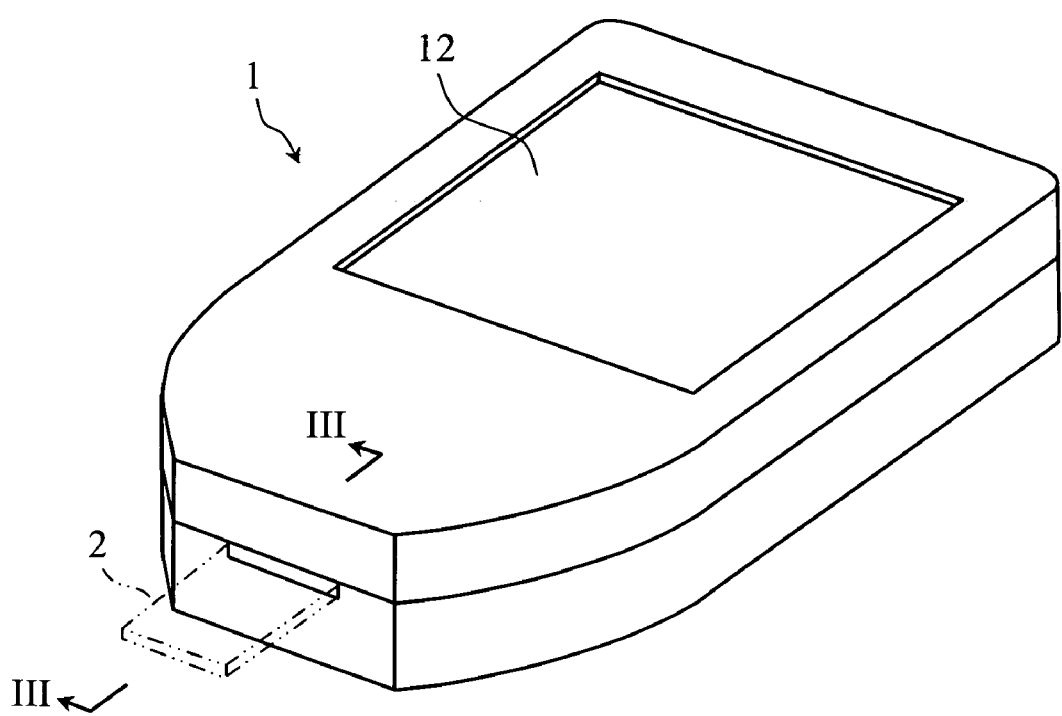

FIG. 1 is an overall perspective view showing one example of a measuring apparatus according to the present invention.

[2]

Figure 2:
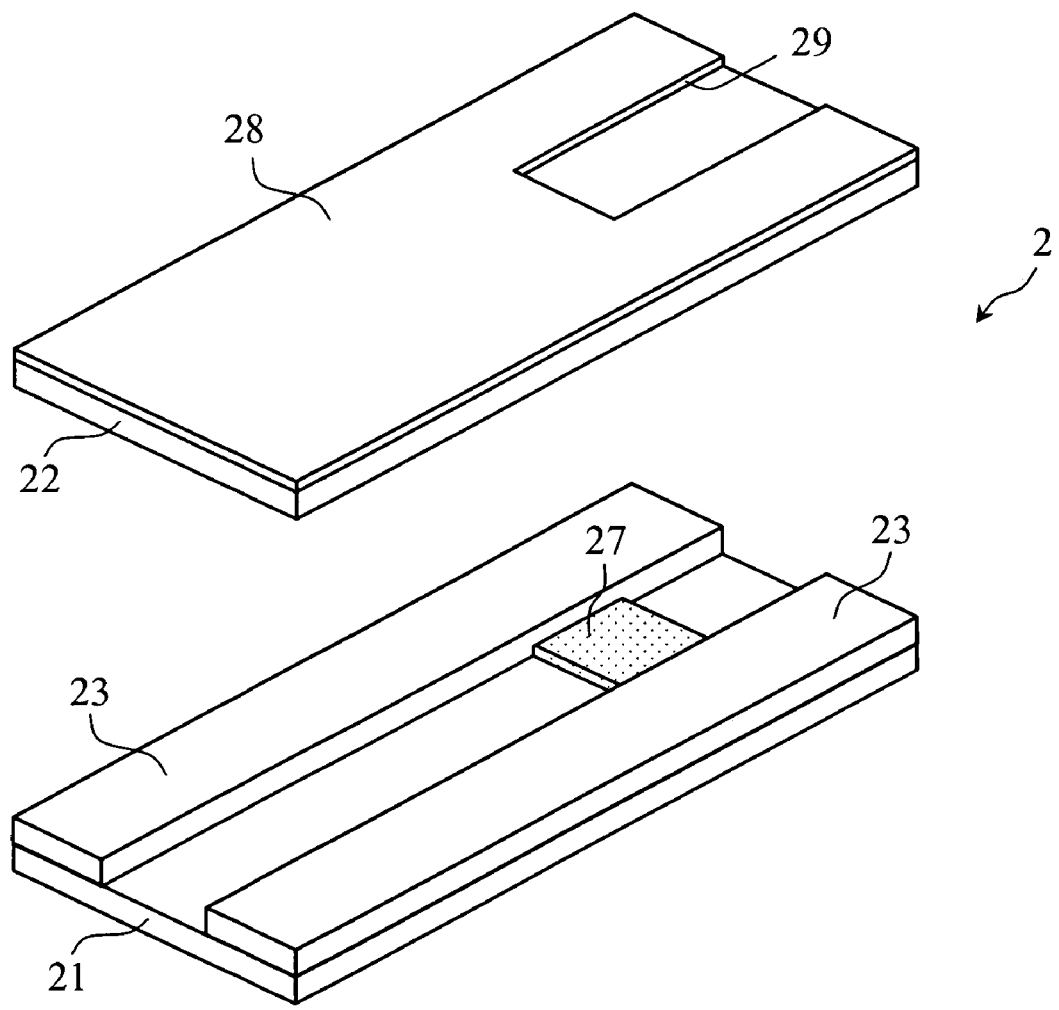

FIG. 2 is a partially exploded perspective view showing one part representing one example of a colorimetric sensor used in the measuring apparatus shown in FIG. 1.

[3]

Figure 3:
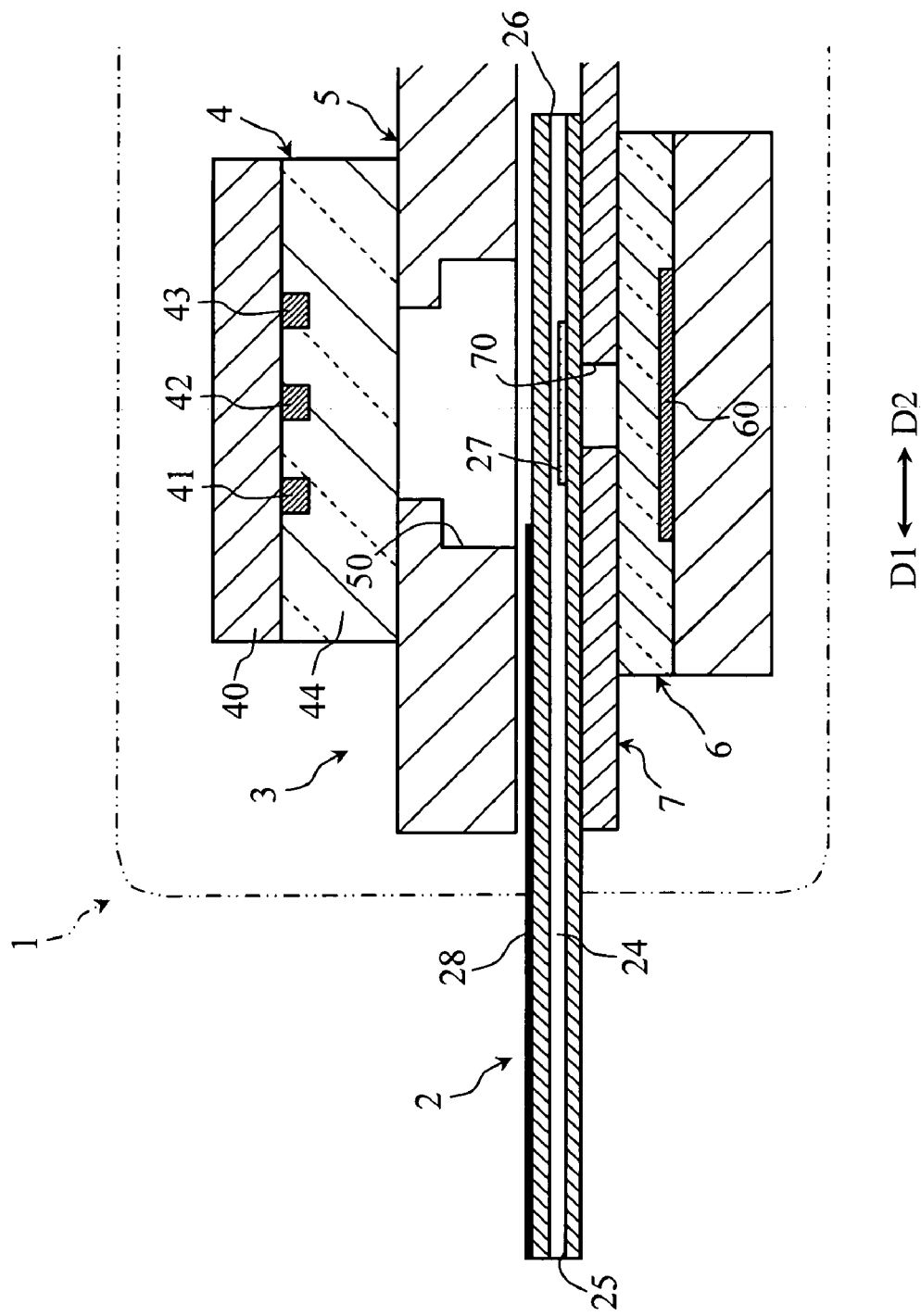

FIG. 3 is a cross-section view along a line III-III in FIG. 1.

[4]

Figure 4:
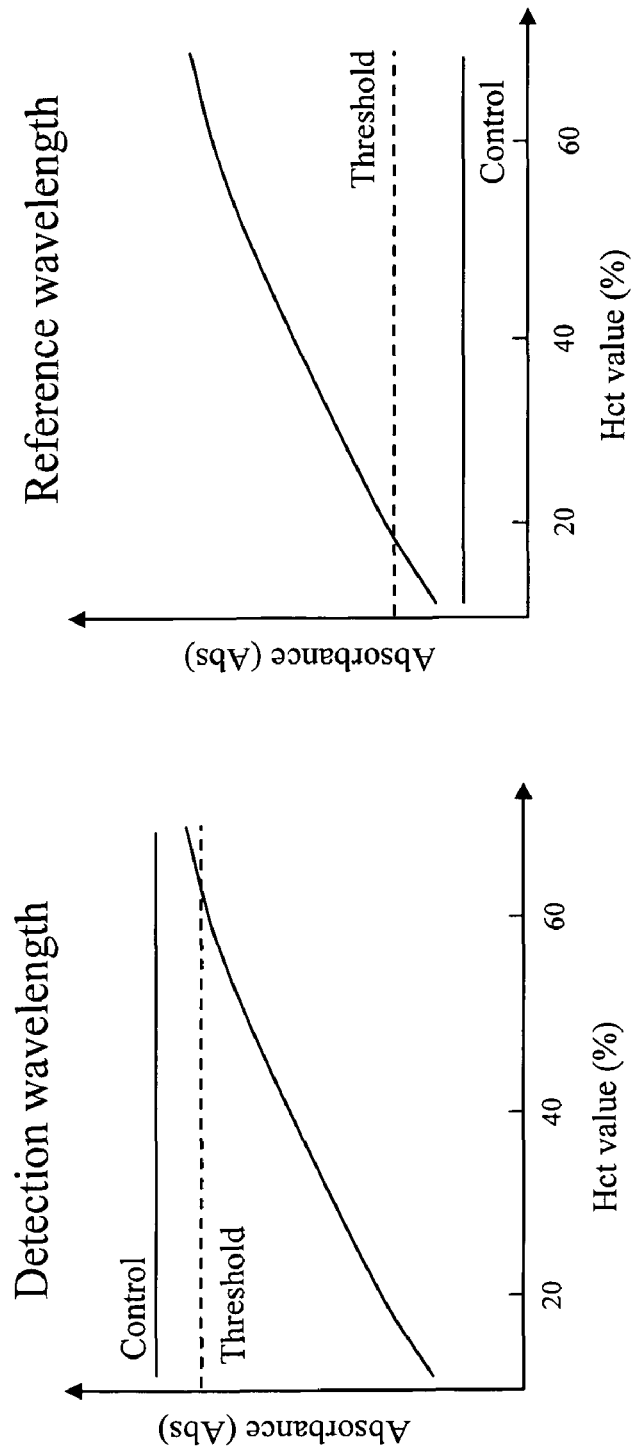

FIG. 4A is a graph schematically showing absorbance when luminance of whole blood is measured at a detection wavelength, as a relation with a hematocrit value, and FIG. 4B is a graph schematically showing absorbance when the luminance of the whole blood is measured at a reference wavelength, as the relation with a hematocrit value.

[5]

Figure 5:
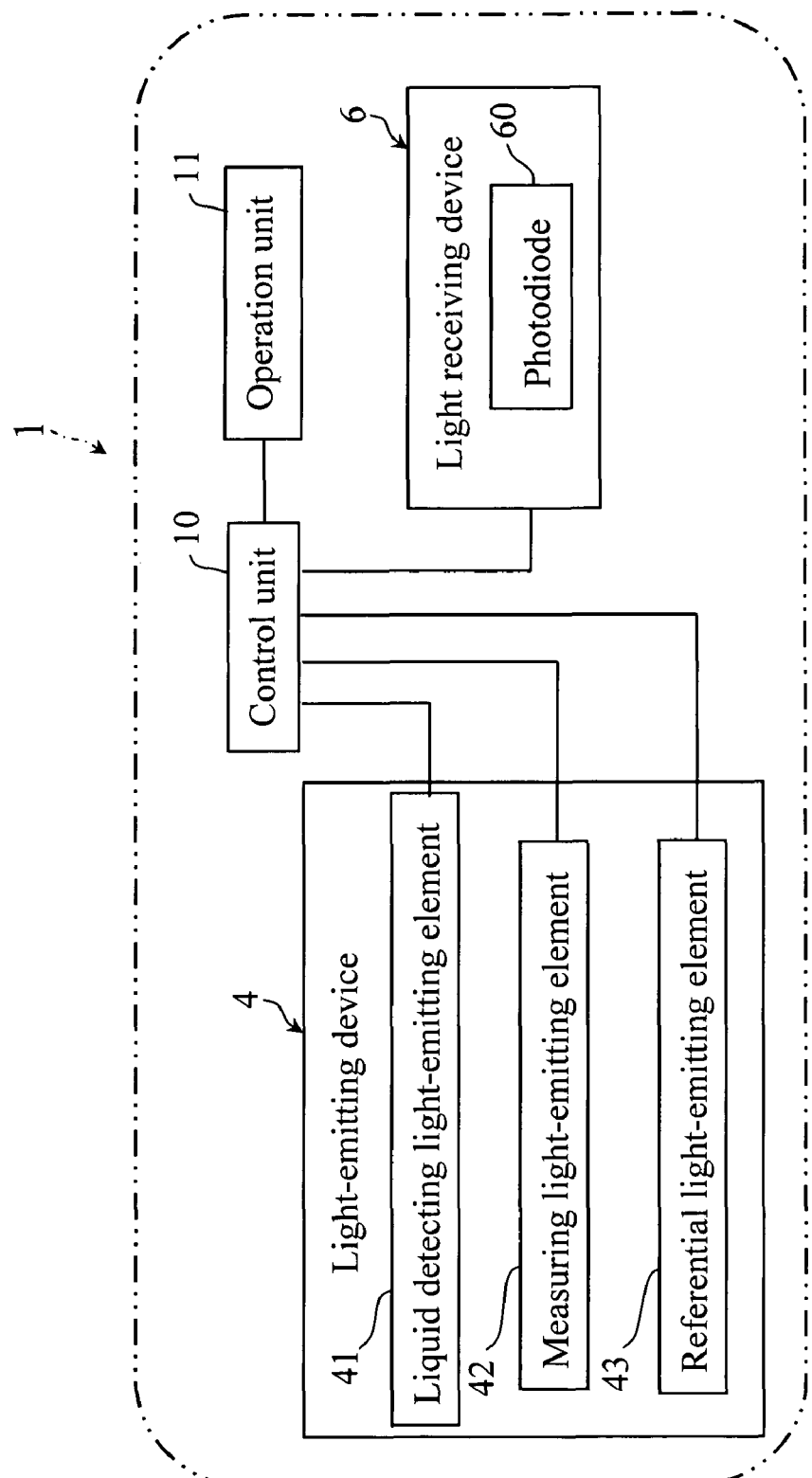

FIG. 5 is a block diagram explaining an essential part of the measuring apparatus shown in FIG. 1.

[6]

Figure 6:
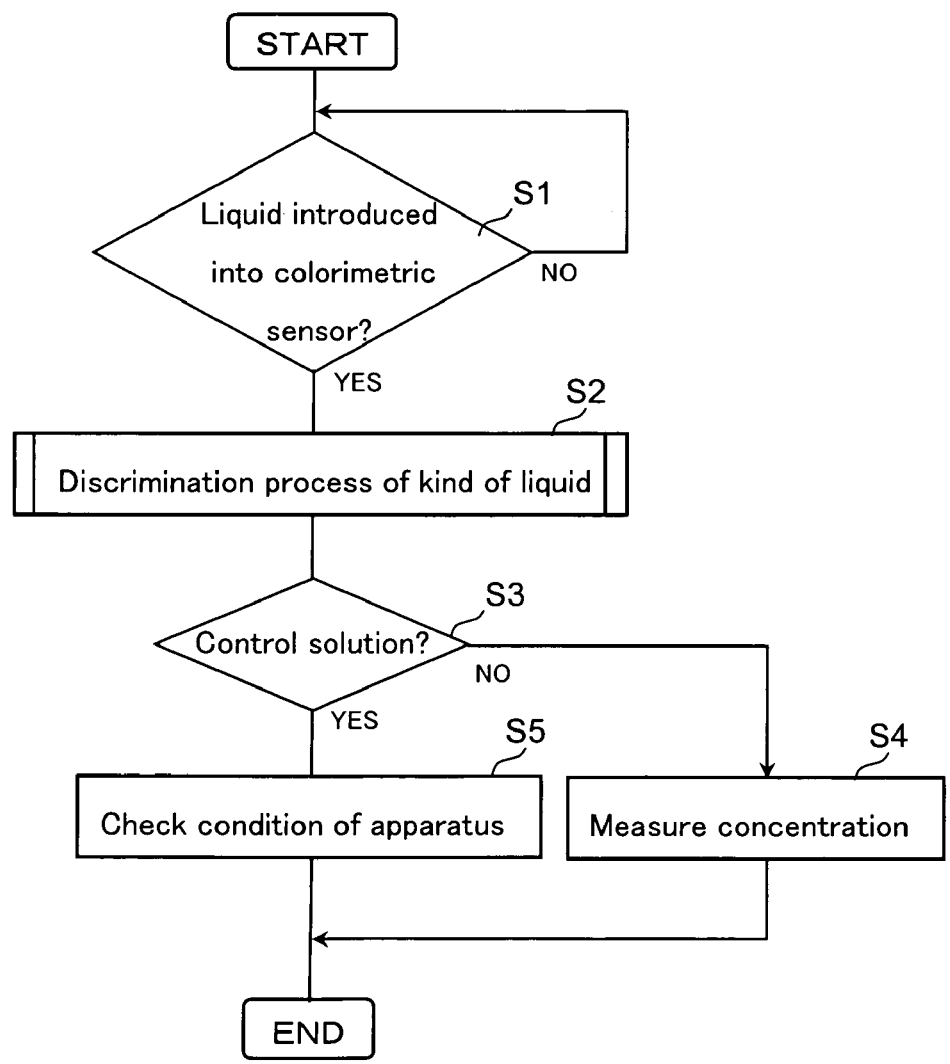

FIG. 6 is a flow chart explaining operation of the measuring apparatus shown in FIG. 1.

[7]

Figure 7:
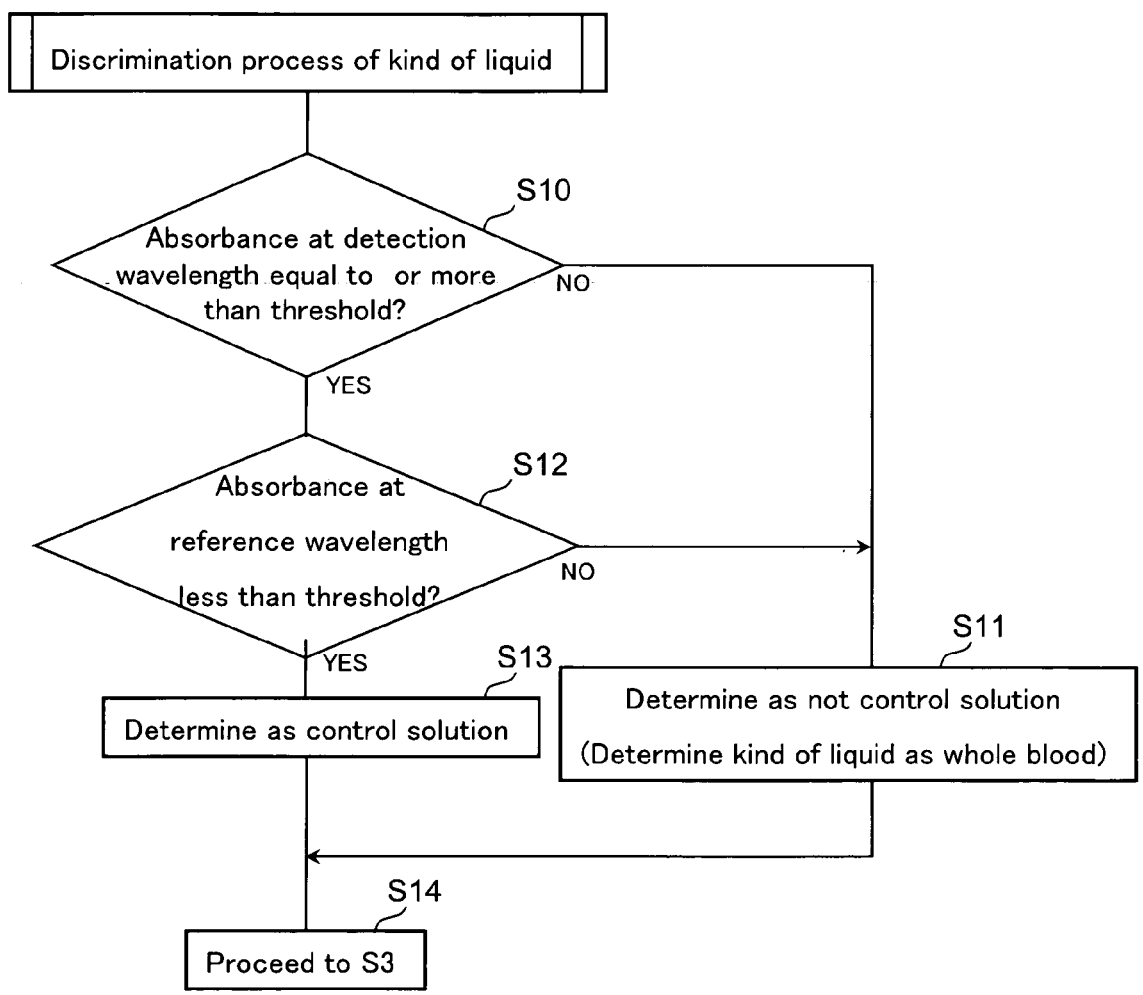

FIG. 7 is a flow chart explaining a process for discriminating whether or not a liquid introduced into the colorimetric sensor is a whole blood or a control solution.

[8]

Figure 8B:
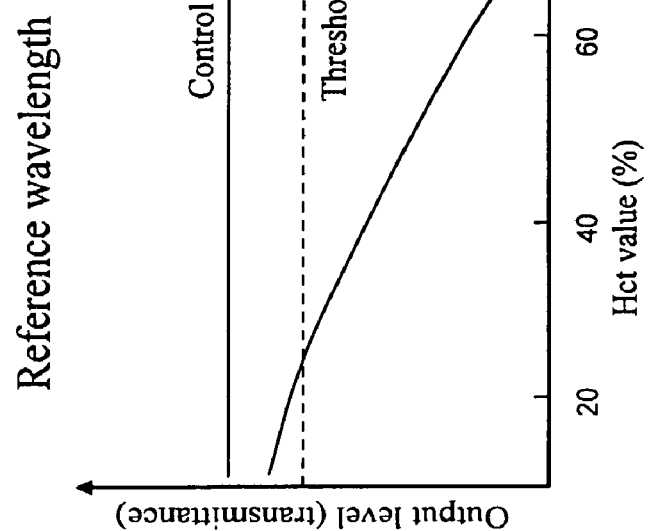
Figure 8A:
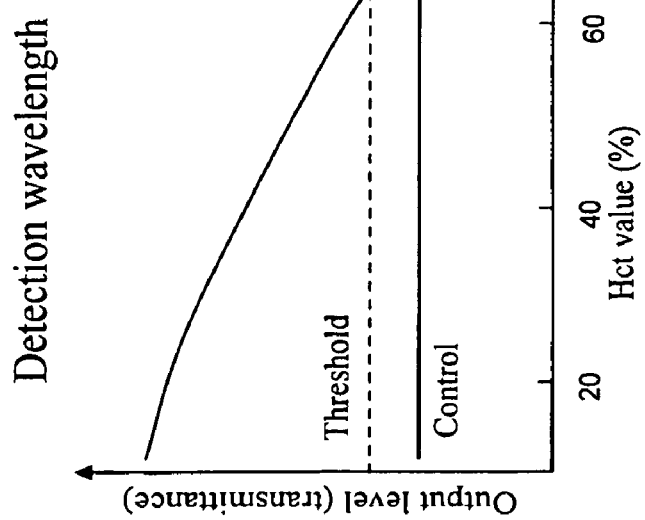

FIG. 8A is a graph schematically showing an output level of photodiode (transmittance) when the luminance of the whole blood is measured at the detection wavelength, as the relation with a hematocrit value, and FIG. 8B is a graph schematically showing an output level of photodiode (transmittance) when the luminance of the whole blood is measured at the reference wavelength, as the relation with a hematocrit value.

[9]

Figure 9:
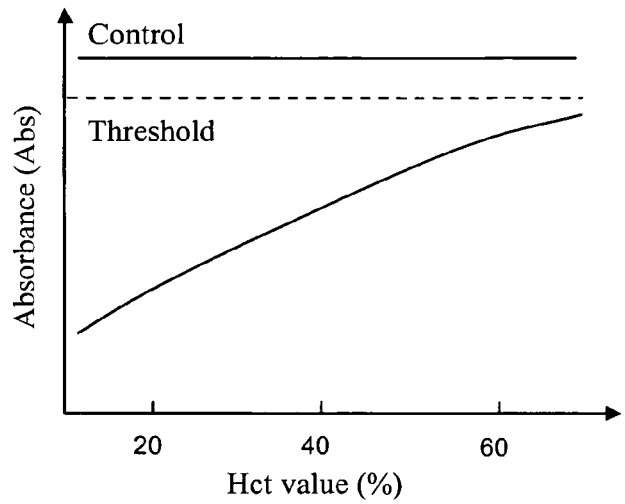

FIG. 9 is a graph schematically showing absorbance when the luminance of the whole blood is measured at the reference wavelength, as the relation with a hematocrit value, for explaining another method for discriminating a control solution.

[10]

Figure 10:
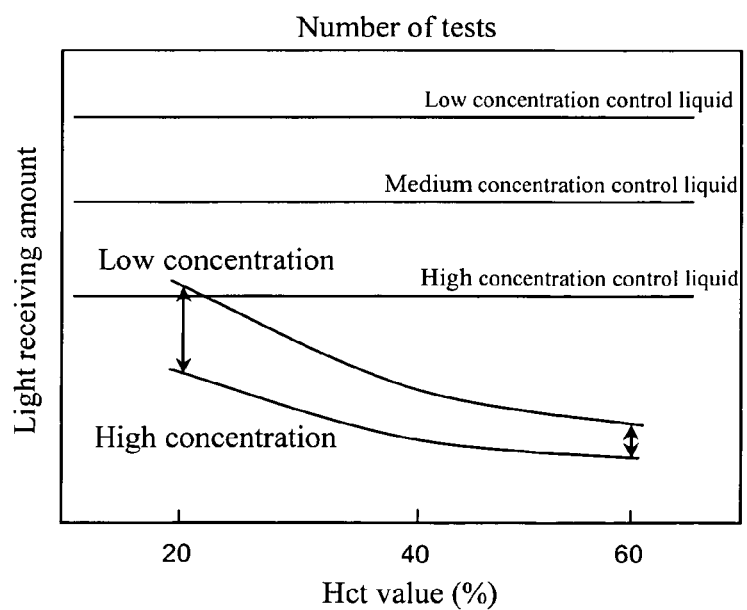

FIG. 10 is a graph schematically showing a light receiving amount when the luminance of the whole blood is measured at the detection wavelength, as the relation with a hematocrit value, for explaining the other method for discriminating a control solution.

[11]

Figure 11:
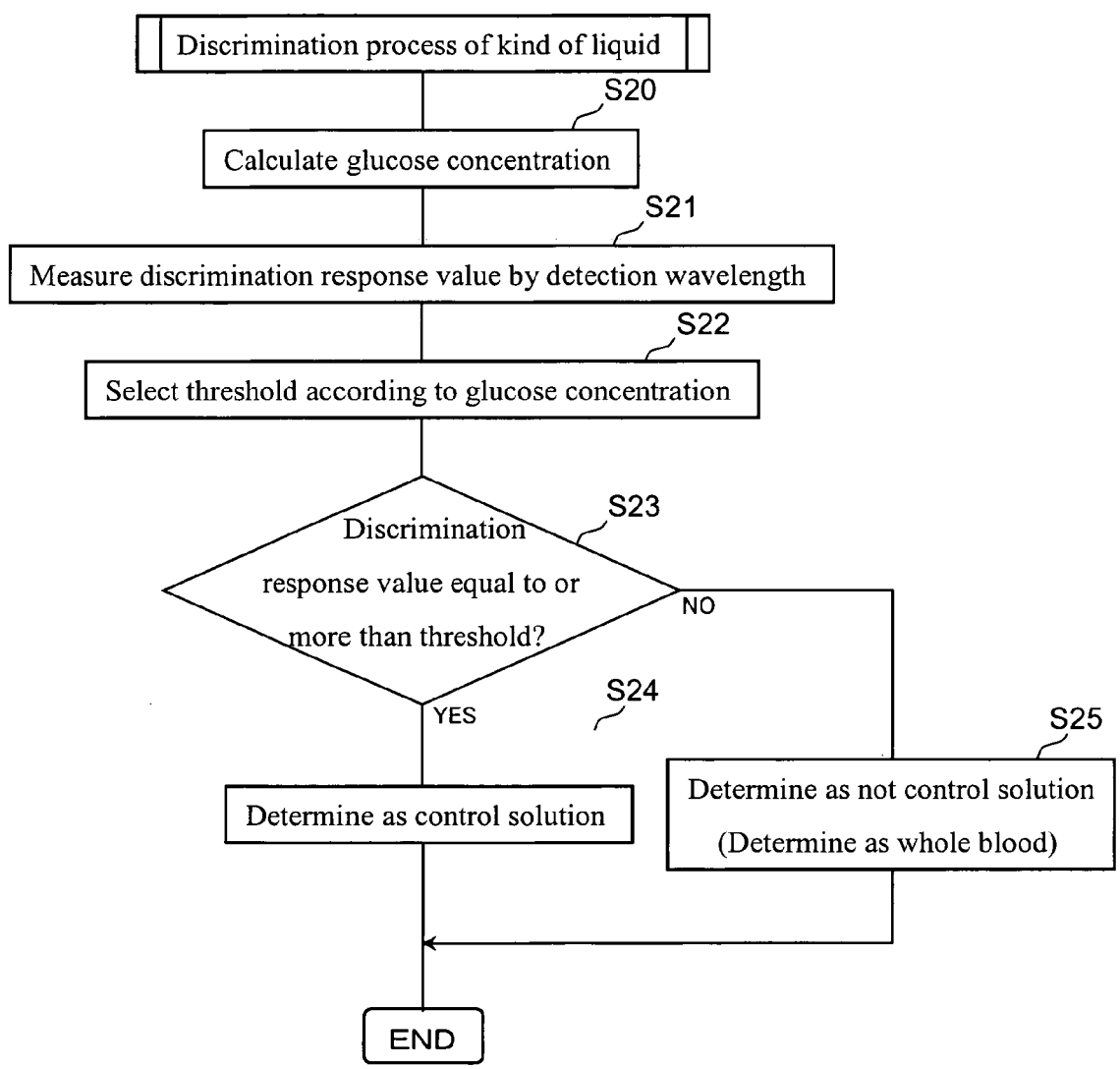

FIG. 11 is a flow chart explaining the other method for discriminating a control solution.

[12]

Figure 12A:
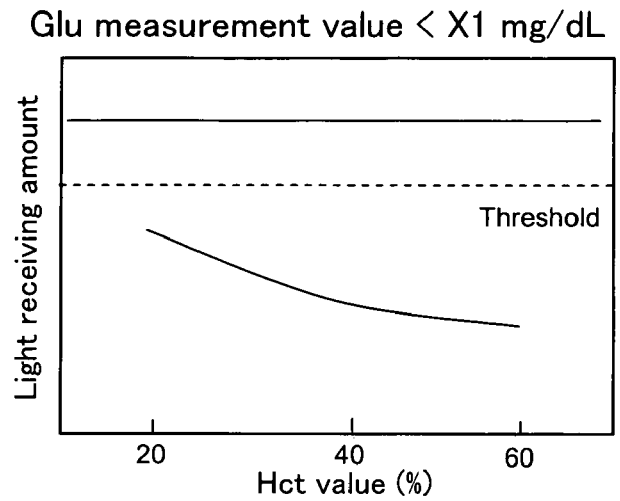
Figure 12B:
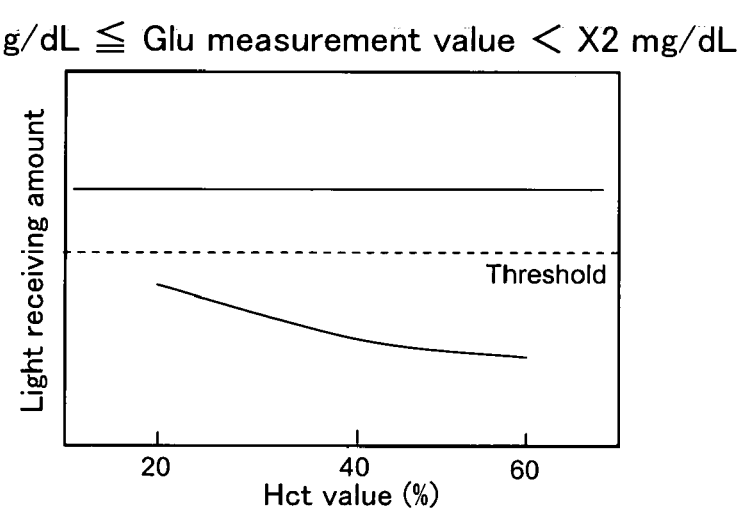
Figure 12C:
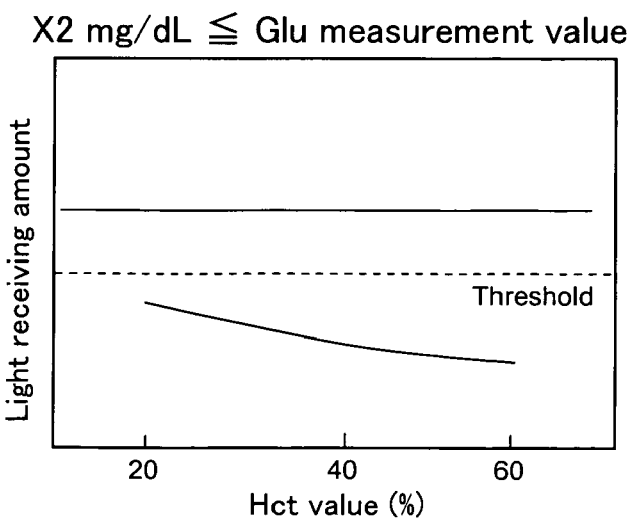

FIG. 12 is a graph schematically showing a light receiving amount when the luminance of the whole blood is measured at the detection wavelength, as the relation with a hematocrit value, for explaining the other method of discriminating a control solution.

[13]

Figure 13:
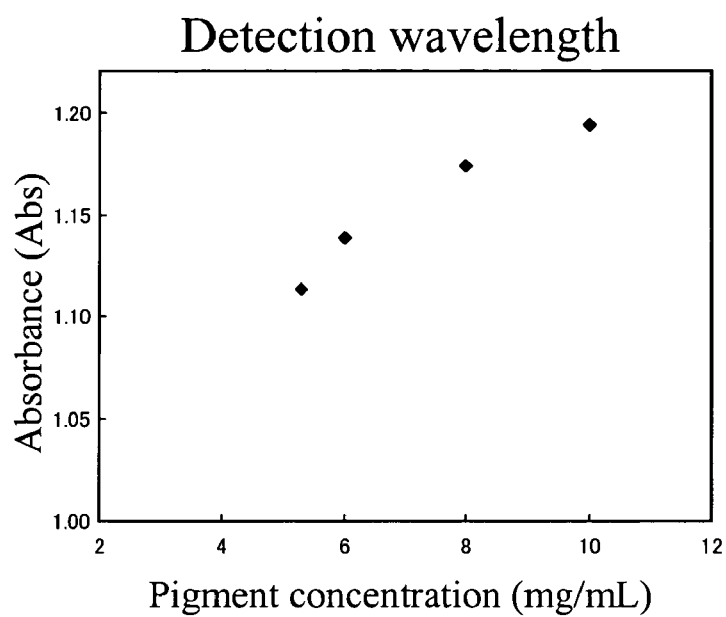

FIG. 13 is a graph showing a measurement result of absorbance in Example 1.

[14]

Figure 14:
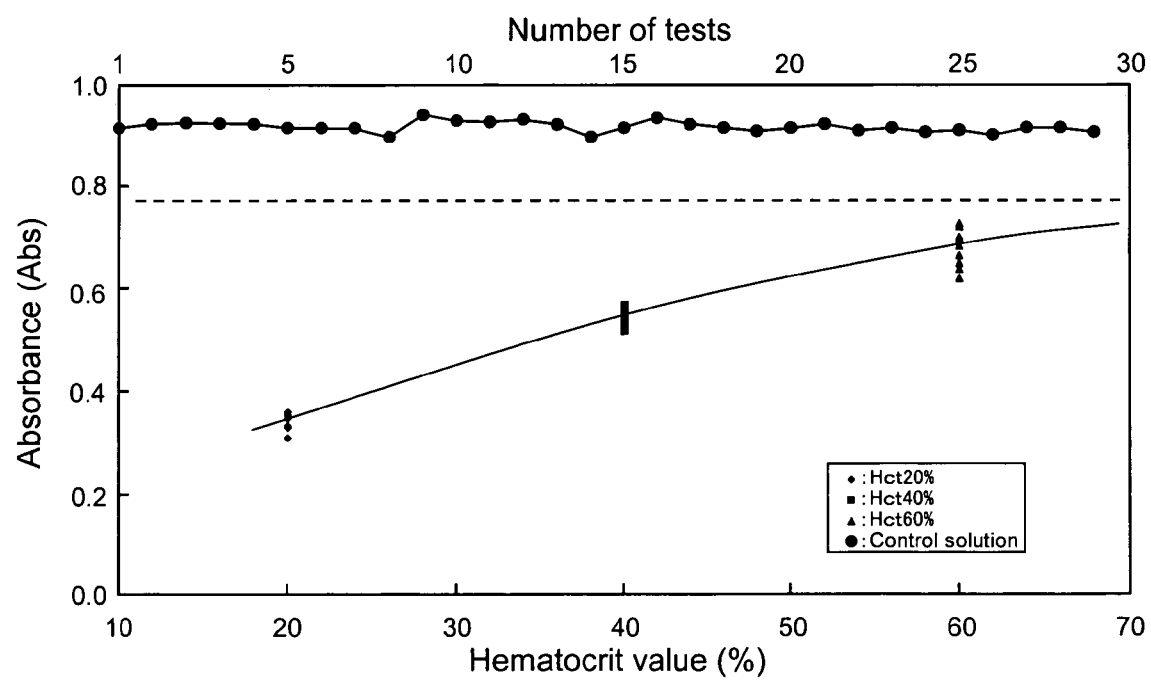

FIG. 14 is a graph showing a measurement result of absorbance in Example 2.

[15]

Figure 15:
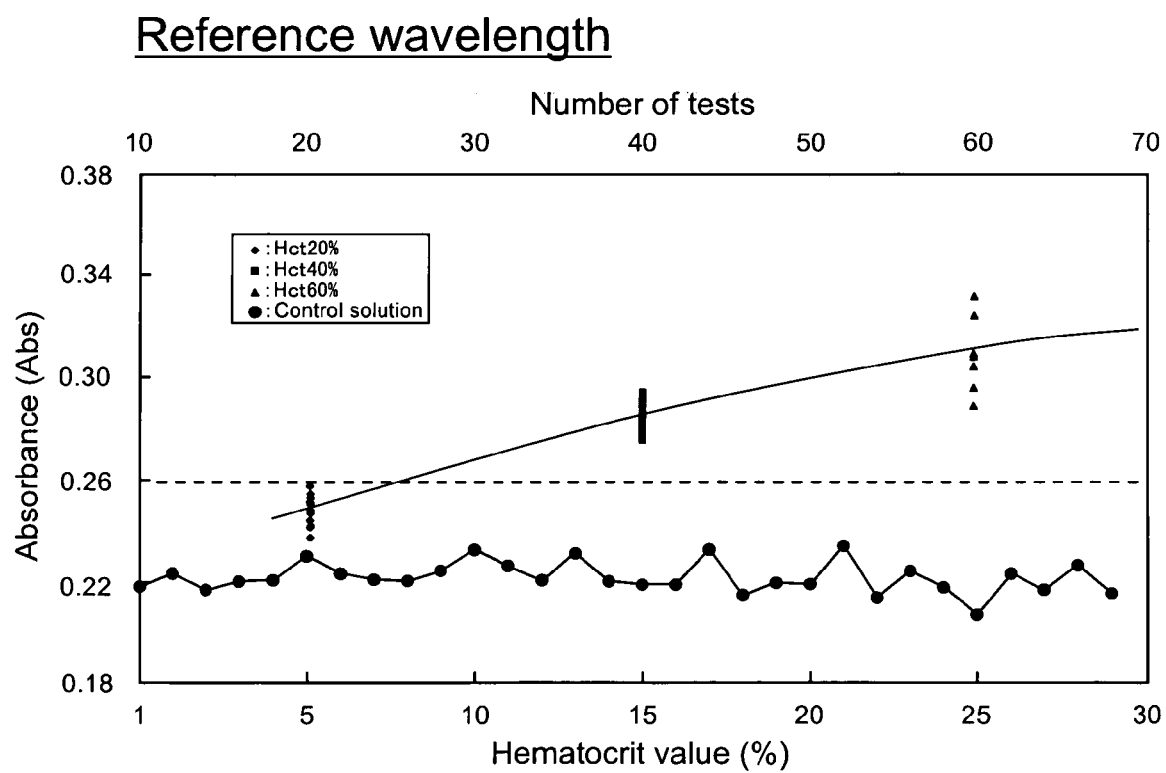

FIG. 15 is a graph showing a measurement result of absorbance in Example 3.

[16]

FIG. 16 is a graph showing a measurement result of a light receiving amount in Example 4.

EXPLANATION OF REFERENCE NUMERALS

1 Concentration measuring apparatus
10 Control unit
11 Operation unit
3 Light-measuring mechanism
41 Liquid detecting light-emitting element
42 Measuring light-emitting element
43 Referential light-emitting element

BEST MODE FOR CARRYING OUT THE INVENTION

Hereinafter, the present invention will be concretely described with reference to attached drawings.

A concentration measuring apparatus 1 shown in FIG. 1 is configured to measure concentration of a target ingredient (for example, glucose, cholesterol or lactic acid) in whole blood using a colorimetric sensor 2.

The colorimetric sensor 2 is configured to be able to analyze blood according to an optical technique using a micro amount, about 0.1 to 3 µL, of blood, and is formed as a disposable sensor. As shown in FIG. 2 and FIG. 3, the colorimetric sensor 2 exhibits a plate-like form as a whole, and is in a form such that long rectangular first and second plate members 21 and 22 are joined by a pair of spacers 23.

This colorimetric sensor 2 has a capillary 24 for retaining blood. The capillary 24 is able to absorb blood by capillary force, and is defined by each of elements 21 to 23. The capillary 24 communicates with the external via an opening 25 for introducing blood inside the capillary 24 and an opening 26 for discharging the air inside the capillary 24. In such a capillary 24, the blood supplied via the opening 25 is absorbed by capillary force arising inside the capillary 24, and moved toward the opening 26.

The first plate member 21 is formed, for example, of PET, PMMA, vinylon, so as to be transparent, and is provided with a reagent part 27 on its surface. The reagent part 27 is disposed inside the capillary 24, and is configured to contain a color coupler. The reagent part 27 is formed, for example, into a solid form that is easy to be dissolved in a blood sample. In such a reagent part 27, when a blood sample is introduced into the capillary 24, the reagent part 27 is dissolved by the blood sample, so that a liquid phase reaction system containing blood and the color coupler is constructed inside the capillary 24. Of course, the reagent part 27 may be such a structure that the color coupler is immobilized to the first plate member 21 using a cross-linking gel or the like.

As the color coupler, various known ones may be used, and those having an absorption wavelength at the time of coloring by giving and receiving of electrons deviated from absorption wavelength of the blood sample (erythrocyte) are preferably used. As such a color coupler, for example, WST-4(2-benzothiazoyl-3-[4-carboxy-2-methoxyphenyl]-5-[4-(2-sulfoethylcarbamoyl)-phenyl]-2H-tetrazolium) or MTT(3-(4,5-dimethyl-2-thiazolyl)-2,5-diphenyl-2H-tetrazolium bromide) may be used.

The reagent part 27 may be configured to further contain an electron transfer substance or an oxidation-reduction enzyme. This makes it possible to achieve giving or receiving of electrons between a target ingredient in a blood sample and the color coupler more quickly, and hence to reduce measurement time. The electron transfer substance or the oxidation-reduction enzyme may be provided separately from the reagent part 27.

The second plate member 22 is formed, for example, of PET, PMMA, vinylon, so as to be transparent, and is provided with a mask 28 on its surface. The mask 28 is provided for limiting incidence of noise light into the colorimetric sensor 2, while permitting the light outgoing from light-emitting elements 41, 42, and 43 in a light-measuring mechanism 3 as will be described later to enter inside the colorimetric sensor 2, and has a slit 29. The slit 29 is formed to extend along the capillary 24 directly above the reagent part 27. Such a mask 29 may be formed by a known film forming technique such as screen printing using a paste material containing a black pigment, for example.

As shown in FIG. 3, the concentration measuring apparatus 1 has the light-measuring mechanism 3 for obtaining information correlated with concentration of a target ingredient in blood and information concerning a control solution by an optical technique. The light-measuring mechanism 3 is formed into a transmission type, and has a light-emitting device 4, an outgoing aperture 5, a light receiving device 6 and a light receiving aperture 7.

The light-emitting device 4 is provided for emitting light to the colorimetric sensor 2, and is positioned directly above the reagent part 27 of the colorimetric sensor 2 in a condition that the colorimetric sensor 2 is installed in a concentration measuring apparatus 1. The light-emitting device 4 is formed by sealing the three light-emitting elements 41, 42, and 43 mounted on a wiring substrate 40 so that they line up in moving directions D1 and D2 of blood in the capillary 24 of the colorimetric sensor 2, with a translucent resin 44. The translucent resin 44 may be omitted in the light-emitting device 4.

The three light-emitting elements 41 to 43 include a liquid detecting light-emitting element 41, a measuring light-emitting element 42 and a referential light-emitting element 43, and are configured to be driven (light on/off) individually by wirings patterned on the wiring substrate 40.

The liquid detecting light-emitting element 41 is used for detecting introduction of whole blood or a control solution into the colorimetric sensor 2, or for discriminating whether or not the liquid introduced into the colorimetric sensor 2 is whole blood or a control solution. As the liquid detecting light-emitting element 41, for example, a LED is used, however those capable of outputting light having a peak wavelength within the wavelength range (500 to 600 nm) in which absorption in blood (erythrocyte) is high are preferably used.

The measuring light-emitting element 42 is used for obtaining information correlated with concentration of a target ingredient in blood. As the measuring light-emitting element 42, a LED capable of outputting light having a peak wavelength in the wavelength range where absorption at the color coupler is high, namely in a wavelength range of 600 to 700 nm, for example is used.

The referential light-emitting element 43 is used for discriminating whether or not the liquid introduced into the colorimetric sensor 2 is a whole blood or a control solution so as to obtain information for removing the influence of turbidity or scattering of whole blood. As the referential light-emitting element 43, a LED capable of outputting light having a peak wavelength in a wavelength range of, for example, 700 to 950 nm, and preferably 800 to 950 nm is used.

As described above, each of the liquid detecting light-emitting element 41 and the referential light-emitting element 43 is also used for the purpose of discriminating a control solution. When the wavelengths within the ranges as exemplified above are selected as the detection wavelength and the reference wavelength, a control solution having an absorbance higher than an upper limit value of absorbance supposed when luminance of the whole blood is measured by the liquid detecting light-emitting element 41 (detection wavelength) and having an absorbance lower than an lower limit value of absorbance supposed when the luminance of the whole blood is measured by the referential light-emitting element 43 (reference wavelength) is used. For example, when height (cell length) of the capillary 24 of the colorimetric sensor 2 is set at 40 to 60 μm, a control solution prepared so as to have absorbance at a detection wavelength of 0.75 Abs or higher, preferably 1.0 Abs or higher, and absorbance at a reference wavelength of less than 0.26 Abs, preferably less than 0.22 Abs is used. Such a control solution is prepared, for example, as a solution containing a red pigment, and having a maximum absorption wavelength ranging from 500 to 600 nm.

As the red pigment, at least one selected from 6-hydroxy-5-(2-methoxy-5-methyl-4-sulfophenylazo)-2-naphthalene sulfonic acid, 7-hydroxy-8-(4-sulfonaphthylazo)-1,3-naphthalene disulfonic acid, and 3',6'-bis(diethylamino)spiro[3H-2,1-benzoxathiol-1,1-dioxide-3,9'-[9H]xanthene]-6-sulfonic acid may be used. Concentration of the red pigment is selected depending on the kind of using red pigment, and an intended absorption characteristic, and is, for example, 3 to 10 mg/mL.

To the control solution, a buffer, a preservative, a viscosity modifier, a dispersing agent, or a foam inhibitor in addition to the red pigment may be added, and the absorption characteristic may be modified depending on an additive.

Here as shown in FIG. 4A and FIG. 4B, absorbance of whole blood increases with a hematocrit value both in the cases of the detection wavelength and the reference wavelength. On the other hand, a hematocrit value of whole blood is about 20 to 70%. Therefore, by preparing a control solution so that absorbance of the control solution is higher than an upper limit value of absorbance supposed when the luminance of the whole blood is measured at the detection wavelength (for example, absorbance at a hematocrit value of 70%), it is possible to discriminate the control solution from the whole blood. On the other hand, by preparing the control solution so that absorbance of the control solution is lower than a lower limit value of absorbance supposed when the luminance of the whole blood is measured at the reference wavelength (for example, absorbance at a hematocrit value of 20%), it is possible to discriminate the control solution from the whole blood. As is apparent from FIG. 4A, in the case of the detection wavelength, the lower the hematocrit value, the higher the difference in absorbance between the control solution and whole blood is, while as is apparent from FIG. 4B, in the case of the reference wavelength, the higher the hematocrit value, the higher the difference in absorbance between the control solution and whole blood is. Discrimination by using the detection wavelength is suited for discriminating a control solution form a whole blood having a relatively low hematocrit value, while discrimination by using the reference wavelength is suited for discriminating a control solution from whole blood having a relatively high hematocrit value. Therefore, by preparing a control solution to have an absorbance higher than the aforementioned upper limit value, and to have an absorbance lower than the aforementioned lower limit value, and discriminating the kind of liquid introduced into the colorimetric sensor 2 by two kinds of wavelengths, namely a detection wavelength and a reference wavelength, it is possible to reliably discriminate the control solution from whole blood regardless of a hematocrit value of whole blood.

As shown in FIG. 3, the outgoing aperture 5 is provided for defining light to be emitted to the colorimetric sensor 2, and is arranged to be located between the light-emitting device 4 and the colorimetric sensor 2 in a condition that the colorimetric sensor 2 is installed in the concentration measuring apparatus 1. The outgoing aperture 5 has an opening 50, and is formed to be black as a whole, for example, of a resin or the like. The opening 50 has an oval planar view shape, and is configured to control a light emission state to the colorimetric sensor 2 by allowing the light emitted from each of the light-emitting elements 41 to 43 to transmit through the opening 50.

The light receiving device 6 is provided for receiving light having transmitted through the colorimetric sensor 2, and is arranged so that it is opposed to the light-emitting device 4 and is positioned directly below the reagent part 27 of the colorimetric sensor 2 in a condition that the colorimetric sensor 2 is installed in the concentration measuring apparatus 1. The light receiving device 6 has a photodiode 60.

The light receiving aperture 7 is provided for defining light to be entered the photodiode 60, and is arranged so that it is located between the colorimetric sensor 2 and the light receiving device 6 in a condition that the colorimetric sensor 2 is installed in the concentration measuring apparatus 1. The light receiving aperture 7 has an opening 70, and is formed to be black as a whole, for example, of a resin or the like.

The concentration measuring apparatus 1 further includes a control unit 10 and an operation unit 11 in addition to the light-measuring mechanism 3, as shown in FIG. 5.

The control unit 10 controls various operations including lighting on/off of each of the light-emitting elements 41 to 43 and operation of the operation unit 11.

The operation unit 11 executes operation for discriminating whether or not the liquid supplied to the colorimetric sensor 2 is whole blood or a control solution based on a light receiving amount of the photodiode 60, and calculates concentration of a target ingredient in blood. The operation unit 11 is configured to execute operations concerning hematocrit correction, Lot correction and temperature correction as is necessary.

Next, one example of operation of the concentration measuring apparatus 1 will be described.

As shown in flowchart of FIG. 6, in the concentration measuring apparatus 1, when the colorimetric sensor 2 is installed, first, whether or not a liquid is supplied to the colorimetric sensor 2 is determined (S1). This determination is made by measuring luminance of a light-measuring region in the colorimetric sensor 2 (the part corresponding to the reagent part 27) with the use of the liquid detecting light-emitting element 41. In other words, when a-liquid is supplied to the colorimetric sensor 2, the capillary 24 is filled with the liquid by the capillary force arising in the capillary 24 of the colorimetric sensor 2, so that absorbance in the light-measuring region increases. Therefore, it is possible to detect whether or not a liquid is introduced to the colorimetric sensor 2 based on the absorbance in the light-measuring region. The absorbance in the light-measuring region may be obtained by calculating output from the photodiode 60 in the operation unit 11.

When it is determined that a liquid is supplied to the colorimetric sensor 2 (S1: YES), the control unit 10 determines which one of whole blood and the control solution, the liquid supplied to the colorimetric sensor 2 is (S2). This determination is conducted in the sequence shown in the flowchart of FIG. 7.

First, the control unit 10 determines whether or not the absorbance of the liquid obtained with the use of the liquid detecting light-emitting element 41 (detection wavelength) is equal to or higher than a threshold (S10). As absorbance for this determination, absorbance obtained in S1 of FIG. 6 may be used. It is also possible that apart from S1, the absorbance of the liquid may be measured with the use of the liquid detecting light-emitting element 41 for the purpose of discriminating the kind of the liquid. On the other hand, the threshold in S10 is set at an upper limit value of absorbance supposed when luminance of whole blood is measured at the detection wavelength. That is, as shown in FIG. 4A, the threshold is set at an absorbance when the hematocrit value is 70% or at a value close to the same.

In S10 of FIG. 7, when it is determined that the absorbance at the detection wavelength is not equal to or more than the threshold (S10: NO), the control unit 10 determines that the liquid introduced to the colorimetric sensor 2 is not a control solution (is a whole blood) (S11).

On the other hand, when it is determined that the absorbance of the liquid at the detection wavelength is equal to or more than the threshold (S10: YES), the control unit 10 determines whether or not the absorbance of liquid at the reference wavelength is less than a threshold (S12). The absorbance for this determination may be obtained by calculating output from the photodiode 60 in the operation unit 11 when the light-measuring region of the colorimetric sensor 2 is irradiated with light from the referential light-emitting element 43 (reference wavelength). On the other hand, the threshold in S12 is set at a lower limit value of the absorbance supposed when the luminance of the whole blood is measured at the reference wavelength. That is, as shown in FIG. 4B, the threshold is set at an absorbance at a hematocrit value of 20% or a value close to the same.

By the way, when the absorbance of the liquid at the detection wavelength is equal to or more than the threshold, a possibility that the liquid is a control solution is high, however, as is prospected from anticipated from FIG. 4A, there is a possibility that the liquid is whole blood having a large hematocrit value. In particular, when a measurement error is taken in consideration, it is difficult to conclude that the liquid is a control solution. On the other hand, as is apparent from FIG. 4B, in the light-measuring at the reference wavelength, it is easy to discriminate a control solution from whole blood having a large hematocrit value, and hence in S11, it is determined whether or not the liquid introduced into the colorimetric sensor 2 is a whole blood having a large hematocrit value or a control solution.

In S12 of FIG. 7, when it is determined that the absorbance at the reference wavelength is not less than the threshold (S12: NO), the control unit 10 determines that the liquid introduced into the colorimetric sensor 2 is not a control solution (is a whole blood)(S11).

On the other hand, when it is determined in S12 that the absorbance at the reference wavelength is less than the threshold (S12: YES), the control unit 10 determines that the liquid introduced into the colorimetric sensor 2 is a control solution (S13).

When the kind of the liquid is discriminated in S11 or in S13, the flow proceeds to S3 in the flowchart shown in FIG. 6 (S14).

In S3, the control unit 10 determines whether the kind of the liquid discriminated in S11 or in S13 is the control solution or not. In S3, when the control unit 10 determines that the kind of the liquid is not a control solution (is a whole blood) (S3: NO), the concentration of a target ingredient in whole blood is measured (S4).

Measurement of concentration is carried out based on output from the photodiode 60 when the light-measuring region of the colorimetric sensor 2 is irradiated with the light from the measuring light-emitting element 42 and the referential light-emitting element 43. More concretely, the absorbance of whole blood when the light-measuring region is irradiated with light from the measuring light-emitting element 42 is calculated in the operation unit 11 based on the output from the photodiode 60. Similarly, the absorbance when the referential light-emitting element 43 is used is calculated in the operation unit 11. The operation unit 11 further calculates absorbance for concentration calculation from which influence of turbidity and scattering in whole blood is removed by subtracting an absorbance at the referential light-emitting element 43 from the absorbance by the measuring light-emitting element 42. Next, the operation unit 11 calculates concentration of a target ingredient in whole blood by fitting the previously calculated absorbance for concentration calculation, to a calibration curve determined in advance.

On the other hand, when it is determined that the kind of the liquid is a control solution (S3: YES), the control unit 10 checks the condition of the apparatus by measuring luminance of the control solution (S5). This check is performed in a similar manner as a usual concentration measurement, and it is determined that the apparatus normally operates when the concentration obtained at this time falls within a predetermined range, while it is determined that the apparatus has some abnormality when the concentration does not fall within the predetermined range. When it is determined that the apparatus has some abnormality, calibration of the apparatus may be performed. Calibration of the apparatus may be achieved, for example, by calibrating a calibration curve used for calculation of concentration of a target ingredient according to a measurement result of concentration of the control solution.

In the measuring apparatus 1, discrimination between whole blood and a control solution is automatically performed. Therefore, in measurement of a control solution, it is not necessary for a user to select a mode for measuring a control solution, so that a burden on the user is mitigated. Further by adapting to perform discrimination of the control solution automatically, such a situation will not occur that an operation check is performed without switching the mode from the normal measurement mode to the control solution measurement mode, or that measurement of a sample is performed without switching the mode from the control measurement mode to the normal measurement mode. As a result, an accurate check result or measurement result is obtainable, so that the necessity of re-check or re-measurement is less likely to occur.

Further, since the measuring apparatus 1 does not discriminate the control solution according to profile of reflectance, it is less likely to be influenced by dissolubility and reaction speed of the reagent part 27. Therefore, it is possible to accurately discriminate a control solution in mutual colorimetric sensors 2 between which there is variation in dissolubility or reaction speed of the reagent part 27, or in mutual colorimetric sensors 2 between which there is a time lag from production to use.

In the measuring apparatus 1, since discrimination of the control solution is performed with the use of the liquid detecting light-emitting element 41 and the referential light-emitting element 43, it is possible to impart a function capable of discriminating the control solution in a cost effective manner, without adding a new element to the light-measuring mechanism 3.

The present invention is not limited to the embodiments as described above. For example, the light-measuring mechanism 3 is not necessarily configured to discriminate the control solution based on the light having transmitted the colorimetric sensor 2, but may be configured to discriminate the control solution based on the light reflected at an analytical tool such as the colorimetric sensor 2.

Further, the operation unit 11 is not necessarily configured to discriminate the control solution by absorbance, and may be configured to perform calculation for discriminating the control solution based on transmittance or reflectance, information correlated therewith, or information correlated with absorbance. For example, the operation unit 11 may discriminate the control solution based on an output level (transmittance) from the photodiode 60 as shown in FIG. 8A and FIG. 8B. In contrast to absorbance, the output level (transmittance) decreases with increase in a hematocrit value both in the cases of the detection wavelength and the reference wavelength. Therefore, a control solution having an output level (transmittance) less than the lower limit value of an output level (transmittance) supposed when luminance of whole blood is measured by the detection wavelength (for example, the value when the hematocrit value is 70%), and having an output level higher than the upper limit value of an output level (transmittance) supposed when the luminance of the whole blood is measured by the reference wavelength (for example, the value when the hematocrit value is 20%) is used. As such a control solution, a solution similar to that used in discriminating a control solution based on absorbance may be used.

The operation unit 11 may discriminate the control solution by either one of the liquid detecting light-emitting element 41 and the referential light-emitting element 43. That is, the control solution may be discriminated in either one of step S10 and step S12 in FIG. 7, and of course, the control solution may be discriminated by either one of the detection wavelength and the reference wavelength when the control solution is discriminated based on the output level (transmittance) of the photodiode 60.

Further, as shown in FIG. 9, it is also possible to discriminate a control solution from whole blood by using a control solution having an absorbance at the reference wavelength higher than the upper limit value of absorbance supposed when luminance of whole blood is measured at the reference wavelength. That is, discrimination between whole blood and a control solution may be made according to whether the absorbance at the reference wavelength, of the liquid introduced into the colorimetric sensor 2 is equal to or higher than the threshold.

The threshold is set to be an absorbance at hematocrit value of 70% or a value close to the same. Here, when the height (cell length) of the capillary 24 of the colorimetric sensor 2 is set at 40 to 60 μm, the threshold is set, for example, at 0.50 Abs or higher, preferably 0.70 Abs or higher.

As the control solution having an absorbance higher than the aforementioned threshold in the reference wavelength, for example, a solution containing an IR pigment having higher light absorption in a near infrared region may be used. As the IR pigment, a quinoline quinine metal complex, a nickel dithiolene pigment, a nickel tetramine pigment, a quinine pigment, a phthalocyanine pigment, a naphthocyanine pigment, and a specialty azo pigment can be exemplified. Further, the concentration of the IR pigment is selected depending on the kind of the using IR pigment and an intended transmission characteristic, and is for example, 000.1 to 0.005 mg/dL.

Next, another example of the discriminating method of the present invention will be described with reference to FIG. 10 to FIG. 12.

In the discriminating method described below uses as a control solution, a low concentration control solution having a relatively low concentration of a target ingredient, a high concentration control solution having a relatively high concentration of a target ingredient, and a medium concentration control solution having a concentration of a target ingredient between that of the low concentration control solution and that of the high concentration control solution.

In the composition of the control solution, as for concentrations of ingredients other than the target ingredient, for example, a red pigment, a buffer, a preservative, a viscosity modifier, a dispersing agent, or a foam inhibitor may be contained as is the same with the control solution described above.

Here, as shown in FIG. 10, when luminance of whole blood is measured at the detection wavelength, a light receiving amount as a response value decreases with increase in a hematocrit value, and increases with decrease in concentration of the target ingredient. On the other hand, since the hematocrit value of whole blood is about 20 to 70%, the upper limit value of a light receiving amount supposed when the luminance of the whole blood is measured at the detection wavelength is achieved when the hematocrit value is about 20% and the concentration of target ingredient is a low concentration.

On the other hand, a light receiving amount when luminance of the control solution is measured at the detection wavelength increases with decrease in a concentration of the target ingredient in the control solution. Therefore, as for the upper limit value of a light receiving amount supposed when the luminance of the whole blood is measured at the detection wavelength, it may be difficult to make discrimination from that for the high concentration control solution.

In light of this, in the present invention, first, the concentration of a target ingredient in a liquid to be detected (whole blood or control solution) is measured based on a light receiving amount when luminance is measured at the measurement wavelength. The concentration of the target ingredient in this case is preferably obtained as a solution that is not subjected to correction such as hematocrit correction, Lot correction and temperature correction for convenience of calculation and in light of the possibility that the liquid to be detected is a control solution.

Next, by comparing a threshold that is set in advance in accordance with the measured concentration of a target ingredient with a response value such as a light receiving amount measured at the detection wavelength, discrimination between whole blood and a control solution is made. More concretely, when the concentration of a target ingredient is a low concentration, a threshold for a low concentration region is compared with a response value, and when the concentration of a target ingredient is a medium concentration, a threshold for a medium concentration region is compared with a response value, and when the concentration of a target ingredient is a high concentration, a threshold for high a concentration region is compared with a response value.

The threshold for low concentration is set to be a lower value than a response value obtained when luminance of a low concentration control solution is measured when the response value is a light receiving amount. The threshold for low concentration is also set to be a value higher than an upper limit value where a supposed response value reaches maximum when the concentration of a target ingredient in whole blood is measured (response at low concentration of a target ingredient and a low hematocrit value of blood).

The threshold for medium concentration is set to be a lower value than a response value obtained when luminance of a medium concentration control solution is measured when the response value is a light receiving amount. The threshold for medium concentration is also set to be a value higher than the measured concentration of the whole blood exhibiting the largest response value (upper limit value) of the whole blood determined as medium concentration when the concentration of a target ingredient in whole blood is measured. The upper limit value in this case is slightly lower than a boundary concentration between the low concentration and the medium concentration when correction such as hematocrit correction is not performed. That is, a measurement value before correction tends to be enhanced under the influence of a hematocrit value or the like. This may result in that a measurement value after correction (plasma value) is higher than a boundary value even when a measurement value before correction is lower than the boundary concentration.

The threshold for high concentration is set to be a lower value than a response value obtained when luminance of a high concentration control solution is measured when the response value is a light receiving amount. The threshold for high concentration is also set to be a value higher than the measured concentration (upper limit value) of the whole blood exhibiting the largest response value of the whole blood determined as high concentration when the concentration of a target ingredient in whole blood is measured. The upper limit value in this case is made slightly lower than a boundary concentration between the medium concentration and the high concentration in consideration of enhancement of a value under the influence of hematocrit when correction such as hematocrit correction is not performed.

Next, a threshold selected according to a measured concentration before correction is compared with a response value such as a light receiving amount measured at the detection wavelength. In the case where the response value is a light receiving amount, the liquid to be detected is discriminated as a control solution when the response value is higher than the threshold, and the condition of the apparatus is checked. On the other hand, when the response value is lower than the threshold, the liquid to be detected is discriminated as whole blood, and the concentration of a target ingredient in the whole blood is calculated. This calculation may be obtained by correction on a result of concentration calculation that is performed previously.

Next, a process of discriminating a kind of liquid will be described with reference to FIG. 11 and FIG. 12A to FIG. 12C and the like, while taking the case of measuring glucose concentration in whole blood as an example.

First, glucose concentration in a liquid to be detected is measured (S20). Glucose concentration is measured based on a light receiving amount of the photodiode 60 when the colorimetric sensor 2 is irradiated with light by means of the measuring light-emitting element 42 (measurement wavelength) (see FIG. 3). The glucose concentration in this case is calculated without performing any corrections including hematocrit correction, Lot correction and temperature correction.

Then, a discrimination response value for discriminating the kind of liquid by the detection wavelength is measured (S21). The discrimination response value is measured based on a light receiving amount of the photodiode 60 when the colorimetric sensor 2 is irradiated with light by means of, for example, the liquid detecting light-emitting element 41 (detection wavelength) (see FIG. 3). As the discrimination response value, a value after a lapse of a certain time (for example, after 1 to 10 second(s), typically after about 5 seconds) from when the liquid to be detected is ascertained to be supplied to the colorimetric sensor 2 is employed. As the discrimination response value, it is preferred to employ a value obtained by dividing an actually measured response value by a blank response value in the condition that the liquid to be detected is not supplied to the colorimetric sensor 2.

Next, a threshold is selected depending on the glucose concentration measured in S20 (S22). Glucose concentration is classified into a low concentration, a medium concentration, or a high concentration in advance, as shown, for example, in FIG. 12A to FIG. 12C, and a threshold assigned to that each classification is selected.

Here, when glucose concentration in whole blood is measured, the concentration of the low concentration control solution is set, for example, at 20 to 50 mg/dL (typically about 35 mg/dL), the concentration of the medium concentration control solution is set, for example, at 90 to 125 mg/dL (typically about 107 mg/dL), and the concentration of the high concentration control solution is set, for example, at 250 to 320 mg/dL (typically, about 285 mg/dL).

On the other hand, a boundary value in classifying a liquid to be detected according to the glucose concentration is appropriately set depending on the concentration of the control solution, and a boundary value X1 between the low concentration and the medium concentration is set, for example, at 50 to 96 mg/dL (typically, about 80 mg/dL), and a boundary value X2 between the medium concentration and the high concentration is set, for example, at 144 to 280 mg/dL (typically, about 250 mg/dL).

Next, by comparing the selected threshold, with a discrimination response value such as light receiving amount measured by the detection wavelength, discrimination between whole blood and a control solution is made (S23). More concretely, when the glucose concentration is a low concentration (concentration lower than X1), comparison is made between a threshold for a low concentration region and the discrimination response value. When the glucose concentration is a medium concentration (concentration equal to or higher than X1 and equal to or lower than X2), comparison is made between a threshold for a medium concentration region and the discrimination response value. When the glucose concentration is a high concentration (concentration equal to or higher than X2), comparison is made between a threshold for a high concentration region and the discrimination response value.

When the discrimination response value is higher than the selected threshold (S23: YES), it is determined that the liquid to be detected is a control solution (S24), while when the discrimination response value is not higher than the selected threshold (S23: NO), it is determined that the liquid to be detected is a whole blood (S25). When it is determined that the liquid to be detected is a control solution, and the apparatus has abnormality, calibration of the apparatus may be performed. Calibration of the apparatus may be performed, for example, by calibrating the calibration curve used for calculation of concentration of a target ingredient according to a concentration measurement result of the control solution.

In the measuring apparatus adopting the discriminating method described above, since discrimination between whole blood and a control solution is automatically performed, a burden on the user is mitigated, and a correct check result and a measurement result are obtained, and the necessity of re-check or re-measurement is less likely to arise.

Further, since the discriminating method described above does not discriminate the control solution by profile of reflectance, it is possible to accurately discriminate the control solution in mutual colorimetric sensors between which there is variation in dissolubility or reaction speed of the reagent part, or in mutual colorimetric sensors between which there is a time lag from production to use.

The present invention may also be applied not only to a case where concentration measurement is performed by an optical technique using the colorimetric sensor, but also to a case where concentration measurement is performed by an electrochemical technique. In this case, the concentration measuring light-emitting element 42 in the light-measuring mechanism 3 is omitted, and the referential light-emitting element 43 is omitted as is necessary, and a control solution is automatically discriminated by the detecting light-emitting element (using the referential light-emitting element as well, as necessary).

EXAMPLE 1

In Example 1, relationship between concentration of a red pigment in a control solution and absorbance at the detection wavelength was examined, and feasibility of the control solution described above was evaluated.

A control solution was prepared by dissolving a red pigment in distilled water so that the concentration of the red pigment was 5.3 mg/mL, 6.0 mg/mL, 8.0 mg/mL or 10.0 mg/mL. As the red pigment, Food Red No. 106 (available from Tokyo Chemical Industry Co., Ltd.) based on 3',6'-bis(diethylamino)spiro [3H-2,1-benzoxathiol-1,1-dioxide-3',9-[9H]xanthene]-6-sulfonic acid was used.

Absorbance was measured at a measurement wavelength of 570 nm using a spectrophotometer ("No.V-550 visible/ultraviolet spectrophotometer"; available from Jasco Corporation). Cell length in the spectrophotometer was 10 mm, and in the actual measurement, a sample was diluted 100 folds to 2000 folds for actual measurement. Measurement result of absorbance of a control solution is shown in FIG. 13, with respect to concentration of a red pigment, as a horizontal axis.

As is apparent from FIG. 13, absorbance of the control solution exceeds 1.0 Abs in the concentration range measured in the present Example, and is sufficiently usable as a control solution in the detection wavelength. In Example 1, examination was made for a case where 3',6'-bis(diethylamino)spiro [3H-2,1-benzoxathiol-1,1-dioxide-3',9-[9H]xanthene]-6-sulfonic acid was used as a red pigment, however, it can be expected that it is sufficiently useable as a control solution in the detection wavelength even when another red pigment such as 6-hydroxy-5-(2-methoxy-5-methyl-4-sulfophenylazo)-2-naphthalene sulfonic acid or 7-hydroxy-8-(4-sulfonaphthylazo)-1,3-naphthalene disulfonic acid is used as the red pigment.

EXAMPLE 2

In Example 2, in the detection wavelength, absorbance was measured a plurality of times for the control solution, and absorbance was measured a plurality of times for three kinds of whole blood samples having different hematocrit values, and feasibility of the control solution previously described was evaluated.

As the control solution, a solution prepared to have a concentration of a red pigment of 6 mg/mL by using Food Red No. 106 likewise in Example 1 as a red pigment was used. Absorbance of the control solution was measured 30 times.

On the other hand, as the whole blood, those prepared to have hematocrit values of 20%, 40% and 60% were used. Absorbance was measured ten times for each whole blood having the respective hematocrit values.

Absorbance of a control solution and whole blood was measured at the detection wavelength in a similar manner as in Example 1. Measurement result of absorbance was shown in FIG. 14.

As is apparent from FIG. 14, in the detection wavelength, the higher the hematocrit value of whole blood, the higher the absorbance was, and absorbance at a hematocrit value of about 70% was about 0.75 Abs. On the other hand, absorbance of the control solution was about 0.9 Abs, which was higher than the absorbance supposed as absorbance of whole blood at the detection wavelength. Therefore, in Example 2, it was found that by appropriately selecting composition of the control solution, discrimination between whole blood and a control solution can be achieved at the detection wavelength.

EXAMPLE 3

In Example 3, feasibility of the control solution in the reference wavelength was evaluated. Example 3 was conducted in a similar manner as Example 1, except that as the control solution and whole blood, similar ones as used in Example 2 were used, and absorbance was measured at a reference wavelength of 810 nm. Measurement results of absorbance are shown in FIG. 15.

As is apparent from FIG. 15, in the reference wavelength, the higher the hematocrit value of whole blood, the higher the absorbance was, and absorbance at a hematocrit value of about 20% was about 0.25 Abs. On the other hand, absorbance of the control solution was about 0.22 Abs, and was lower than absorbance supposed as absorbance of whole blood at the reference wavelength. Therefore, in Example 3, it was found that by appropriately preparing the control solution, discrimination between whole blood and a control solution can be achieved at the reference wavelength.

From both the result in Example 3 and the result in Example 2, it is possible to discriminate a control solution from whole blood by the control solution of the same composition both in the detection wavelength and in the reference wavelength, and it can be found that discrimination between whole blood and a control solution can be performed more reliably according to absorbance at the detection wavelength and at the reference wavelength. Further, discrimination by the detection wavelength is suited for discrimination between a whole blood having a relatively low hematocrit value and a control solution, and discrimination by the reference wavelength is suited for discrimination between a whole blood having a relatively high hematocrit value and a control solution. Therefore, by taking the results of both of the detection wavelength and the reference wavelength into account, it is possible to securely discriminate a control solution from whole blood irrespective of hematocrit value of the whole blood.

EXAMPLE 4

In Example 4, the ability or disability of discriminating a a plurality of kinds of control solutions having different glucose concentrations from whole blood was evaluated by measuring response values of a control solution and whole blood 30 times, respectively.

Compositions of the control solutions were as shown in Table 1 below.

TABLE 1

| | | |
|---|---|---|
| 1 | | Glucose |
| | | Food Red No. 106 |
| | | PVA500 (partially saponificated type) |
| 2 | | Control solution |
| 3 | | Low concentration |
| 4 | | Medium concentration |
| 5 | | High concentration |

PVA500: available from Wako Pure Chemical Industries, Ltd.
ProClin200: available from SIGMA Co. Ltd.
HEPES: (N-[2-Hydroxyethyl] piperazine-N'-[2-ethanesulfonic acid]

As the whole blood, whole blood prepared from mixed blood samples from three persons by adjusting hematocrit value (Hct) to 20%, and adjusting glucose concentration to 0 mg/dL, 70 mg/dL, or 190 mg/dL was used.

Response value was measured as a light receiving amount when a control solution or blood was supplied to the colorimetric sensor in the condition that the colorimetric sensor (trade name "Q sensor"; ARKRAY Inc.) was installed in the measuring apparatus (trade name "PocketChem Q meter"; ARKRAY Inc.). The light receiving amount was measured as an output count value from the photodiode in the measuring apparatus after 5 seconds from supplying the colorimetric sensor with a control solution or whole blood. Measurement results of light receiving amount are shown FIG. 16A to FIG. 16C, in values (ratio to blank) obtained by division by an output count value (cell blank) in the condition that a control solution or whole blood is not supplied to the colorimetric sensor.

Figure 16A:
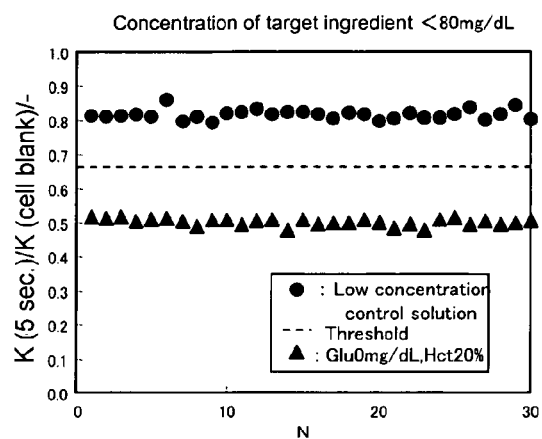

FIG. 16A shows measurement results of light receiving amount for a low concentration control solution having a glucose concentration of 35 mg/dL and for a whole blood having a glucose concentration of 0 mg/dL.

Here, the low concentration control solution having a glucose concentration of 35 mg/dL is a control solution selected as an object to be compared when glucose concentration before correction is low concentration (for example, concentration lower than 80 mg/dL) in the condition that whether the liquid to be detected is a control solution or whole blood is not known. On the other hand, as for whole blood, when glucose concentration before correction is a low concentration, a response value as a light receiving amount is large when glucose concentration is 0 mg/dL, and a hematocrit value in human blood is not less than about 20%. Therefore, the whole blood having a glucose concentration of 0 mg/dL (Hct 20%) has the closest light receiving amount with the low concentration control solution. Therefore, when there is a significant difference between a response value (light receiving amount) of the whole blood having a glucose concentration of 0 mg/dL (Hct 20%) and a response value (light receiving amount) of the low concentration control solution, it is possible to discriminate the low concentration control solution from the whole blood.

As shown in FIG. 16A, in measurements of 30 times, the light receiving amount, as a ratio relative to blank showed approximately a constant value both in the low concentration control solution and in the whole blood. Further, the light receiving amount was higher in the control solution than in the whole blood, and large difference was observed in measurement results of a response value between the low concentration control solution and the whole blood.

In FIG. 16A, an average (0.665) between an average value of measurement result of the control solution and an average value of measurement result of the whole blood is represented by the chain line. Taking the value of this chain line as a threshold, it is possible to discriminate the low concentration control solution from the whole blood when it is determined that glucose concentration of the liquid to be detected is low concentration. Of course, the value represented by the chain line in FIG. 16A is not necessarily set as a threshold, and in the experimental condition of this time, it is possible to discriminate the low concentration control solution from the whole blood when it is determined that glucose concentration of the liquid to be detected is low concentration if the ratio of light receiving amount falls within the range of 0.6 to 0.7, for example.

Figure 16B:
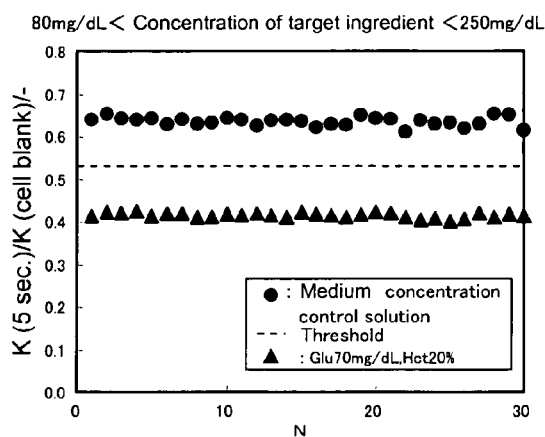

FIG. 16B shows measurement results of a light receiving amount for a medium concentration control solution having a glucose concentration of 107 mg/dL and for a whole blood having a glucose concentration of 70 mg/dL.

Here, the medium concentration control solution having a glucose concentration of 107 mg/dL is a control solution selected as an object to be compared when glucose concentration before correction is medium concentration (for example, concentration equal to or more than 80 mg/dL and less than 250 mg/dL) in the condition that whether the liquid to be detected is a control solution or whole blood is not known. On the other hand, as for whole blood, when glucose concentration before correction is medium concentration, a response value as a light receiving amount is large when glucose concentration is a lower limit of the medium concentration region, and hematocrit value in human blood is not less than about 20%. However, since glucose concentration before correction is measured as an enhanced value when the liquid to be detected is a whole blood, comparison is made between a response value (light receiving amount) of whole blood having a glucose concentration obtained by subtracting a value of expected enhancement from a lower limit of the medium concentration region or a concentration slightly lower than the same (for example, about 70 mg/dL when lower limit is 80 mg/dL) and a response value (light receiving amount) of low concentration control solution, and when there is a significant difference therebetween, it is possible to discriminate the low concentration control solution from the whole blood.

As shown in FIG. 16B, in measurements of 30 times, the light receiving amount, as a ratio relative to blank showed approximately a constant value both in the medium concentration control solution and the whole blood. Further, the light receiving amount was higher in the control solution than in the whole blood, and large difference was observed in measurement results of a response value between the medium concentration control solution and the whole blood.

In FIG. 16B, an average (0.531) between an average value of measurement result of the control solution and an average value of measurement result of the whole blood is represented by the chain line. Taking the value of this chain line as a threshold, it is possible to discriminate the medium concentration control solution from the whole blood when it is determined that glucose concentration of the liquid to be detected is medium concentration. Of course, the value represented by the chain line in FIG. 16B is not necessarily set as a threshold, and in the experimental condition of this time, it is possible to discriminate the medium concentration control solution from the whole blood when it is determined that glucose concentration of the liquid to be detected is medium concentration if the ratio of light receiving amount falls within the range of 0.5 to 0.6, for example.

Figure 16C:
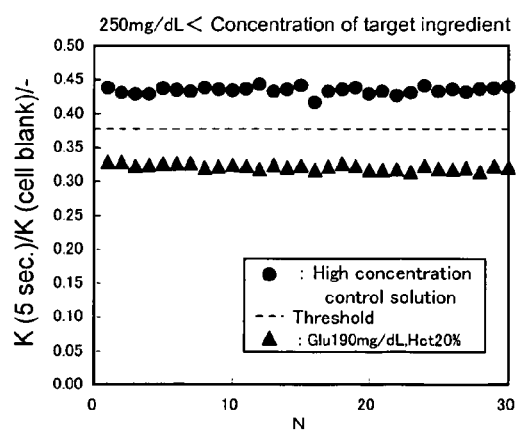

FIG. 16C shows measurement results of light receiving amount for a high concentration control solution having a glucose concentration of 285 mg/dL and for a whole blood having a glucose concentration of 190 mg/dL.

Here, the high concentration control solution having a glucose concentration of 285 mg/dL is a control solution selected as an object to be compared when glucose concentration before correction is a high concentration (for example, concentration equal to or more than 250 mg/dL) in the condition that whether the liquid to be detected is a control solution or whole blood is not known. On the other hand, as for whole blood, when glucose concentration before correction is high concentration, a response value as a light receiving amount is large when glucose concentration is a lower limit of the high concentration region, and hematocrit value in human blood is not less than about 20%. However, since glucose concentration before correction is a measured as an enhanced value when the liquid to be detected is a whole blood, comparison is made between a response value (light receiving amount) of whole blood having a glucose concentration obtained by subtracting a value of expected enhancement from a lower limit of the high concentration region or a concentration slightly lower than the same (for example, about 190 mg/dL when lower limit is 250 mg/dL) and a response value (light receiving amount) of low concentration control solution, and when there is a significant difference therebetween, it is possible to discriminate the high concentration control solution from the whole blood.

As shown in FIG. 16C, in measurements of 30 times, the light receiving amount, as a ratio relative to blank showed approximately a constant value both in the high concentration control solution and the whole blood. Further, the light receiving amount was higher in the control solution than in the whole blood, and large difference was observed in measurement results of a response value between the high concentration control solution and the whole blood.

In FIG. 16C, an average (0.387) between an average value of measurement result of the control solution and an average value of measurement result of the whole blood represented by the chain line. Taking this value of the chain line as a threshold, it is possible to discriminate the high concentration control solution from the whole blood when it is determined that glucose concentration of the liquid to be detected is high concentration. Of course, the value represented by the chain line in FIG. 16C is not necessarily set as a threshold, and in the experimental condition of this time, it is possible to discriminate the high concentration control solution from the whole blood when it is determined that glucose concentration of the liquid to be detected is high concentration if the ratio of light receiving amount falls within the range of 0.35 to 0.40, for example.

As described above, by measuring glucose concentration of a liquid to be detected in advance, and comparing with a threshold selected from the concentration thus measured, it is possible to discriminate a control solution from whole blood. Further, since the threshold is selected for comparison with a control solution corresponding to the glucose concentration measured in advance, when it is determined that the liquid to be detected is a control solution, it is also possible to discriminate whether the control solution is low concentration, medium concentration, or high concentration, from the glucose concentration measured in advance.

What is claimed is:
1. A method for automatically discriminating a control solution from a liquid to be detected in a measurement system for measuring a target ingredient in the liquid to be detected, the method comprising:
measuring luminance of a liquid to be detected at a detection wavelength when a response value is absorbance;
determining whether or not a response value of the liquid to be detected at the detection wavelength is equal to or higher than a predetermined upper limit value;
measuring the luminance of the liquid to be detected at the detection wavelength when it is determined that the response value of the liquid to be detected at the detection wavelength is equal to or higher than the predetermined upper limit value;

determining whether or not the response value of the liquid to be detected at a reference wavelength is lower than a predetermined lower limit value; and discriminating the liquid as a control solution when it is determined that the response value at the reference wavelength of the liquid to be detected is lower than the predetermined lower limit value, wherein the predetermined upper limit value has been determined by measuring plural biological samples at the detection wavelength and taking a highest value of the measured values as the upper limit value, and the predetermined lower limit value has been determined by measuring the plural biological samples at the reference wavelength and taking a lowest value of the measured values as the lower limit value.

2. The method for automatically discriminating a control solution according to claim 1, wherein in the measurement system, whole blood is used as a liquid to be detected, and the detection wavelength is selected from a wavelength range of 500 to 600 nm, and the reference wavelength is selected from a wavelength range of 700 to 950 nm.

3. The method for automatically discriminating a control solution according to claim 2, wherein as the control solution, a control solution containing a red pigment, and having a maximum absorption wavelength within a wavelength range of 500 to 600 nm is used.

4. The method for automatically discriminating a control solution according to claim 3, wherein as the red pigment, at least one selected from 6-hydroxy-5-(2-methoxy-5-methyl-4-sulfophenylazo)-2-naphthalene sulfonic acid, 7-hydroxy-8-(4-sulfonaphthylazo)-1,3-naphthalene disulfonic acid, and 3',6'-bis(diethylamino)spiro [3H-2,1-benzoxathiol-1,1-dioxide-3,9'-[9H]xanthene]-6-sulfonic acid is used.

5. The method for automatically discriminating a control solution according to claim 1, wherein as the control solution, a plurality of control solutions having different concentrations of target ingredients are used.

6. The method for automatically discriminating a control solution according to claim 5, wherein as the control solutions, a low concentration control solution having a relatively low concentration of the target ingredient, a high concentration control solution having a relatively large concentration of the target ingredient, and a medium concentration control solution having an intermediate concentration of the target ingredient between those of the low concentration control solution and the high concentration control solution are used.

7. The method for automatically discriminating a control solution according to claim 6, comprising, in a measurement system for measuring a target ingredient in a liquid to be detected by using a measurement wavelength and detecting whether or not the liquid to be detected is supplied by using a detection wavelength:

a first step of measuring concentration of the target ingredient in the liquid to be detected at the measurement wavelength;

a second step of measuring response of the liquid to be detected by the detection wavelength;

a third step of selecting a corresponding response threshold from a plurality of response thresholds set in advance, according to the concentration of the target ingredient measured in the first step; and a fourth step of determining whether or not the liquid to be detected is a control solution by comparing the response measured in the second step and the response threshold selected in the third step.

8. The method for automatically discriminating a control solution according to claim 7, wherein in the measurement system, the measurement wavelength is selected from a wavelength range of 600 to 700 nm.

9. The method for automatically discriminating a control solution according to claim 7, wherein the third step is performed by selecting a response threshold correlated with a particular classification that the concentration of the target ingredient measured in the first step is determined to belong among a plurality of concentration regions classified by the predetermined concentration thresholds;

the concentration thresholds include a first concentration threshold, which is a concentration between the concentration of the target ingredient in the low concentration control solution and the concentration of the target ingredient in the medium concentration control solution, and a second concentration threshold, which is a concentration between the concentration of the target ingredient in the medium concentration control solution and concentration of the target ingredient in the high concentration control solution; and the response threshold includes a first response threshold for use when the concentration measured in the first step is lower than the first concentration threshold, a second response threshold for use when the concentration measured in the third step is equal to or higher than the first concentration threshold and lower than the second concentration threshold, and a third response threshold for use when the concentration measured in the first step is equal to or higher than the second concentration threshold.

10. A control solution which is used for checking a system in a measurement system for measuring a target ingredient in a liquid to be detected, wherein the control solution has a response value at a reference wavelength of the liquid to be detected being lower than a predetermined lower limit value, and has a response value at a detection wavelength of the liquid to be detected being higher than a predetermined higher limit value, the predetermined upper limit value has been determined by measuring plural biological samples at the detection wavelength and taking a highest value of the measured values as the upper limit value, the predetermined lower limit value has been determined by measuring the plural biological samples at the reference wavelength and taking a lowest value of the measured values as the lower limit value, and whole blood is used as a liquid to be detected, and the detection wavelength is selected from a wavelength range of 500 to 600 nm, and the reference wavelength is selected from a wavelength range of 700 to 950 nm.

11. The control solution according to claim 10, wherein the control solution is configured to be used in the measurement system for measuring a target ingredient in the liquid to be detected by using a measurement wavelength, and in the measurement system, the measurement wavelength is selected from a wavelength range of 600 to 700 nm.

12. The control solution according to claim 10, wherein the control solution contains a red pigment and has a maximum absorption wavelength within a wavelength range of 500 to 600 nm.

13. The control solution according to claim 12, wherein as the red pigment, at least one selected from 6-hydroxy-5-(2-methoxy-5-methyl-4-sulfophenylazo)-2-naphthalene sulfonic acid, 7-hydroxy-8-(4-sulfonaphthylazo)-1,3-naphthalene disulfonic acid, and 3',6'-bis(diethylamino)spiro [3H-2,1-benzoxathiol-1,1-dioxide-3,9'[9H]xanthene]-6-sulfonic acid is used.

14. A measuring apparatus for measuring a target ingredient in a liquid to be detected by using a measurement wavelength and a reference wavelength, wherein the measuring apparatus is configured to discriminate a control solution from the liquid to be detected by using a detection wavelength, the control solution being configured to check the measuring apparatus, and when a response value is absorbance, it is determined that the control solution is supplied when at least one of the following conditions is satisfied:

(1) when the response value measured at the reference wavelength is lower than a predetermined lower limit value, or when information from which it is determined that the response value measured at the reference wavelength is lower than the predetermined lower limit value is obtained;

(2) when the response value measured at the detection wavelength is higher than a predetermined upper limit value, or when information from which it is determined that the response value measured at the detection wavelength is higher than the predetermined upper limit value is obtained; and (3) when the response value measured at the reference wavelength is higher than a predetermined upper limit value, or when information from which it is determined that the response value measured at the reference wavelength is higher than the predetermined upper limit value is obtained, wherein the predetermined upper limit value measured at the detection wavelength has been determined by measuring plural biological samples at the detection wavelength and taking a highest value of the measured values as the upper limit value, the predetermined lower limit value measured at the reference wavelength has been determined by measuring the plural biological samples at the reference wavelength and taking a lowest value of the measured values as the lower limit value, and the predetermined higher limit value measured at the reference wavelength has been determined by measuring the plural biological samples at the reference wavelength and taking a highest value of the measured values as the upper limit value, and wherein the measuring apparatus determines whether a control solution is supplied by executing:

a first step of measuring luminance of a liquid to be detected at the detection wavelength;

a second step of determining whether or not a response value of the liquid to be detected at the detection wavelength is equal to or higher than the predetermined upper limit value;

a third step of measuring the luminance of the liquid to be detected at the reference wavelength when it is determined in the second step that the absorbance of the liquid to be detected at the detection wavelength is equal to or higher than the predetermined upper limit value;

a fourth step of determining whether or not the response value at the reference wavelength of the liquid to be detected is lower than the predetermined lower limit value; and a fifth step of discriminating the liquid as a control solution when it is determined in the fourth step that the absorbance at the reference wavelength of the liquid to be detected is lower than the predetermined lower limit value.

15. The measuring apparatus according to claim 14, configured to measure a target ingredient using whole blood as a liquid to be detected, wherein a wavelength range of 500 to 590nm is employed as the detection wavelength, a wavelength range of 600 to 700 nm is employed as the measurement wavelength and a wavelength range of 700 to 950 nm is employed as the reference wavelength.

16. A measuring apparatus for measuring a target ingredient in a liquid to be detected by using a measurement wavelength, wherein the measuring apparatus is configured to detecting whether the liquid to be detected is a control solution by using a detection wavelength, the control solution being configured to check the measuring apparatus, and the measuring apparatus is configured to execute the following steps when a response value is a light receiving amount:

(1) a first step of measuring concentration of the target ingredient in the liquid to be detected at the measurement wavelength;

(2) a second step of measuring response of the liquid to be detected at the detection wavelength;

(3) a third step of measuring a corresponding response threshold from a plurality of response thresholds set in advance, according to the concentration of the target ingredient measured in the first step; and (4) a fourth step of determining whether or not the liquid to be detected is a control solution by comparing the response measured in the second step and the response threshold selected in the third step, wherein when a plurality of control solutions having different concentrations of target ingredients are used as the control solutions, the third step is performed by selecting a response threshold correlated with a particular classification that the concentration of the target ingredient measured in the first step is determined to belong among a plurality of concentration regions classified by the predetermined concentration thresholds.

17. The measuring apparatus according to claim 16, wherein in a case where a low concentration control solution having a relatively low concentration of target ingredient, a high concentration control solution having a relatively large concentration of target ingredient, and a medium concentration control solution having an intermediate concentration of target ingredient between those of the low concentration control solution and the high concentration control solution are used as the control solutions, the concentration thresholds include a first concentration threshold which is a concentration between the concentration of the target ingredient in the low concentration control solution and the concentration of the target ingredient in the medium concentration control solution, and a second concentration threshold which is a concentration between the concentration of the target ingredient in the medium concentration control solution and the concentration of the target ingredient in the high concentration control solution, and the response threshold includes a first response threshold for use when the concentration measured in the first step is lower than the first concentration threshold, a second response threshold for use when the concentration measured in the third step is equal to or higher than the first concentration threshold and lower than the second concentration threshold, and a third response threshold for use when the concentration measured in the first step is equal to or higher than the second concentration threshold.

* * * * *